(12) United States Patent
Hu

(10) Patent No.: US 12,268,936 B2
(45) Date of Patent: Apr. 8, 2025

(54) EXERCISE RECOMMENDATION METHOD AND APPARATUS ELECTRONIC DEVICE AND COMPUTER-READABLE STORAGE MEDIUM

(71) Applicant: BOE TECHNOLOGY GROUP CO., LTD., Beijing (CN)

(72) Inventor: Yulan Hu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 891 days.

(21) Appl. No.: 17/462,949

(22) Filed: Aug. 31, 2021

(65) Prior Publication Data

US 2022/0249910 A1 Aug. 11, 2022

(30) Foreign Application Priority Data

Feb. 8, 2021 (CN) .......................... 202110171834.9

(51) Int. Cl.
| | |
|---|---|
| A63B 24/00 | (2006.01) |
| G06F 3/0482 | (2013.01) |
| G06F 3/16 | (2006.01) |
| G06F 16/2457 | (2019.01) |
| G06F 16/901 | (2019.01) |

(Continued)

(52) U.S. Cl.
CPC ........ *A63B 24/0075* (2013.01); *G06F 3/0482* (2013.01); *G06F 3/167* (2013.01); *G06F 16/24578* (2019.01); *G06F 16/9024* (2019.01); *G16H 10/20* (2018.01); *G16H 10/60* (2018.01); *G16H 20/30* (2018.01); *G16H 50/20* (2018.01);

(Continued)

(58) Field of Classification Search
None
See application file for complete search history.

(56) References Cited

U.S. PATENT DOCUMENTS

2017/0216671 A1* 8/2017 Wisbey .............. A61B 5/02438

FOREIGN PATENT DOCUMENTS

| CN | 106709002 A | 5/2017 |
|---|---|---|
| CN | 107391908 A | 11/2017 |

(Continued)

OTHER PUBLICATIONS

Shi, Zhen-Xing, "Design and Implementation of Personalized Sports Recommandation System", Computer Technology, May 2020, 62 pages (English Abstract Submitted).

(Continued)

*Primary Examiner* — James B Hull
(74) *Attorney, Agent, or Firm* — Calfee, Halter & Griswold LLP

(57) ABSTRACT

An exercise recommendation method and apparatus are described. The method includes: acquiring basic information of a user; querying a pre-established exercise knowledge graph according to the basic information of the user to obtain a target exercise mode list comprising exercise modes, and an evaluation attribute list comprising evaluation attributes corresponding to the target exercise mode list; determining at least one exercise program according to the target exercise mode list and the evaluation attribute list; performing ranking processing on the at least one exercise program according to the evaluation attribute list to obtain a ranking result; recommending at least one target exercise program according to the ranking result.

20 Claims, 13 Drawing Sheets

(51) Int. Cl.
*G16H 10/20* (2018.01)
*G16H 10/60* (2018.01)
*G16H 20/30* (2018.01)
*G16H 50/20* (2018.01)
*G16H 50/30* (2018.01)
*G16H 50/70* (2018.01)
*A61B 5/00* (2006.01)
G16H 20/60 (2018.01)

(52) U.S. Cl.
CPC ............ *G16H 50/30* (2018.01); *G16H 50/70* (2018.01); *A61B 5/4866* (2013.01); *G16H 20/60* (2018.01)

(56) References Cited

FOREIGN PATENT DOCUMENTS

| CN | 109920510 A | 6/2019 |
| CN | 110391007 A | 10/2019 |
| CN | 106776711 B | 4/2020 |
| CN | 111445978 A | 7/2020 |

OTHER PUBLICATIONS

Zhang, Jing, "Multi-target Prediction Algorithm Based on AdaBoost Regression Tree", Jisuanji Yu Xiandaihua, Sep. 2017, 8 pages (English Abstract Submitted).

* cited by examiner

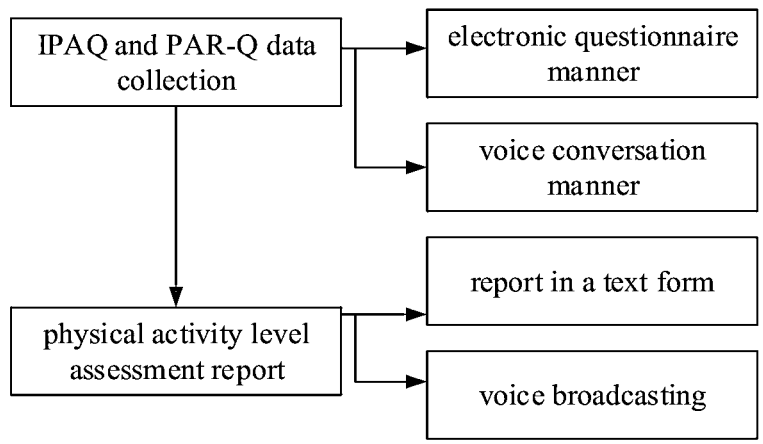

FIG.11

| Exercise category | Exercise name | Calorie consumption | Exercise intensity | MET | Time for 1000-step activity amount |
|---|---|---|---|---|---|
| Chinese traditional exercise | Tai Chi | 240 kcal/h | medium intensity | 4.0 | 8 minutes |
| Chinese traditional exercise | Ba Duan Jin | 270 kcal/h | medium intensity | 4.5 | 7 minutes |
| Chinese traditional exercise | Wu Qin Xi | 240 kcal/h | medium intensity | 4.0 | 8 minutes |
| Chinese traditional exercise | fitness Qigong | 240 kcal/h | medium intensity | 4.0 | 8 minutes |
| Chinese traditional exercise | Yi Jin Jing | 240 kcal/h | medium intensity | 4.0 | 8 minutes |
| Sports activity | bowling | 180 kcal/h | medium intensity | 3.0 | 10 minutes |
| Sports activity | trampoline | 210 kcal/h | medium intensity | 3.5 | 9 minutes |
| Sports activity | pole vault | 360 kcal/h | medium intensity | 6.0 | 5 minutes |
| Sports activity | sandbag hitting | 360 kcal/h | medium intensity | 6.0 | 5 minutes |
| Sports activity | orienteering | 540 kcal/h | high intensity | 9.0 | 3 minutes |

FIG.12

| | calorie calculation | | |
|---|---|---|---|
| weight | 60 | | Kg |
| exercise duration | 40 | | minute |
| exercise mode | bicycle riding（slow speed 16-19.2 km/h ▼ | | | calculate bicycle riding (slow speed, 16-19.2 km/h) the calorie consumption for 40 minutes is: 240 kcal

FIG.13 exercise recommendation-information collection

| | | |
|---|---|---|
| age | 25 | years old |
| gender | ◉ male<br>◎ female | |
| height | 180 | CM |
| weight | 78 | KG |
| waist circumference | 88 | CM | submit

FIG.14

| ▦ | exercise program | | | | ⋀ |
|---|---|---|---|---|---|

| Exercise category | Exercise mode | Exercise duration | Exercise frequency | Exercise intensity |
|---|---|---|---|---|
| aerobic exercise | brisk walking (90~120 steps/min), bicycle riding, pelota, swimming, jogging | 35-50 minutes each time | 5 days a week | 136-156 times/ minute |
| strength exercise | push-ups, weight-bearing heel raising, weight-bearing knee extension, plank, squat up, weight-bearing lift, horse stance, deep squat, back lift, buttock bridge | 15-20 minutes each time | 2 days a week | maximum muscle strength 50%~70% |
| stretch exercise | neck stretch, shoulder stretch, back stretch, chest stretch, abdomen stretch, turning, side leg pressing, side lunge sitting forward bending, lower leg stretch | 5-10 minutes each time | before and after exercise | medium intensity |

Attentions 1. when doing weight loss exercises, each exercise should last 30 to 60 minutes;

2. at the beginning of exercise, the time should be shortened accordingly, preferably not less than 20 minutes/time, and then gradually increased to 45-60 minutes/time to establish a gradual adaptation process;

3. low-intensity, long-term aerobic endurance exercises are mainly taken, supplemented by strength exercises and fitness, achieving the best effect.

FIG.15

| ▦ | Weekly exercise plan | | | | ⋀ |
|---|---|---|---|---|---|

| Days of week | Exercise category | Exercise mode | Exercise duration | METs | Estimated calorie consumption |
|---|---|---|---|---|---|
| Monday | aerobic exercise | swimming | 45 minutes | 8 | 468 kcal |
| Wednesday | aerobic exercise | brisk walking (90-120 steps/ minute) | 45 minutes | 5 | 293 kcal |
| Thursday | aerobic exercise | jogging | 35 minutes | 5.9 | 268 kcal |
| Friday | aerobic exercise | bicycle riding | 45 minutes | 4 | 234 kcal |
| Saturday | aerobic exercise | pelota | 50 minutes | 12 | 781 kcal |
| Thursday | strength exercise | [{"g": "2 groups", "num": "10", "action": "squat up"}, {"g": "2 groups", "num": "10", "action": "squat up"}, {"g": "2~3 groups", "num": "30 seconds", "action": "plank"}, {"g": "2 groups", "num": "5 minutes", "action": "horse stance"}] | 10-15 minutes each time | | |
| Sunday | strength exercise | [{"g": "2~3 groups", "num": "8~12", "action": "weight-bearing lift"}, {"g": "2~3 groups", "num": "8~12", "action": "weight-bearing heel raising"}, {"g": "2~3 groups", "num": "8~12", "action": "deep squat"}, {"g": "2~3 groups", "num": "8~12", "action": "weight-bearing knee extension"}, {"g": "2~3 groups", "num": "8~12", "action": "back lift"}, {"g": "2~3 groups", "num": "8~12", "action": "buttock bridge"}] | 15-20 minutes each time | | |
| | stretch exercise | neck stretch, shoulder stretch, back stretch, chest stretch, abdomen stretch, turning, side leg pressing, side lunge sitting forward bending, lower leg stretch | 5-10 minutes each time | | |

FIG.16

EXERCISE RECOMMENDATION METHOD AND APPARATUS ELECTRONIC DEVICE AND COMPUTER-READABLE STORAGE MEDIUM

RELATED APPLICATION

The present application claims the benefit of Chinese Patent Application No. 202110171834.9 filed on Feb. 8, 2021, the entire disclosure of which is incorporated herein by reference.

FIELD

The present disclosure relates to the technical field of big data processing, particularly to an exercise recommendation method, an exercise recommendation apparatus, an electronic device and a computer-readable storage medium.

BACKGROUND

Sports medicine has attracted more and more concerns and attentions of people. Especially for people with chronic diseases and sub-health, regular and scientific exercises help to maintain health and improve the quality of life. Scientific researches have confirmed that exercise has a positive effect on people with chronic diseases such as diabetes, hypertension, hyperlipidemia, obesity, etc., and helps to improve glucose metabolism, regulate blood pressure, improve blood lipid, reduce and control weight, and so on.

SUMMARY

Some embodiments of the present disclosure provide an exercise recommendation method. The method comprises:
  acquiring basic information of a user;
  querying a pre-established exercise knowledge graph according to the basic information of the user to obtain a target exercise mode list comprising exercise modes, and an evaluation attribute list comprising evaluation attributes corresponding to the target exercise mode list, each of the evaluation attributes indicating an attribute index for evaluating a corresponding exercise mode;
  determining at least one exercise program according to the target exercise mode list and the evaluation attribute list, each exercise program in the at least one exercise program comprising at least one exercise mode and a recommended exercise duration corresponding to the at least one exercise mode;
  performing ranking processing on the at least one exercise program according to the evaluation attribute list to obtain a ranking result;
  recommending at least one target exercise program according to the ranking result.

In some embodiments, said querying a pre-established exercise knowledge graph according to the basic information of the user to obtain a target exercise mode list comprising exercise modes, and an evaluation attribute list comprising evaluation attributes corresponding to the target exercise mode list comprises:
  creating at least one query statement according to the basic information of the user;
  querying the exercise knowledge graph according to each query statement in the at least one query statement respectively to obtain the target exercise mode list and the evaluation attribute list corresponding to the target exercise mode list.

In some embodiments, the basic information of the user comprises: a target disease type of the user, a target user attribute of the user, and a physical activity level assessment result of the user, and
  wherein said creating at least one query statement according to the basic information of the user comprises:
  acquiring a physical activity level assessment result of the user;
  in response to the physical activity level assessment result of the user being a high level, creating a first query statement using the target user attribute and the target disease type as query conditions;
  in response to the physical activity level assessment result of the user being a medium level or below, creating a first query statement using the target user attribute and the target disease type as query conditions, and creating a second query statement using the physical activity level assessment result of the user as a query condition.

In some embodiments, the exercise knowledge graph comprises a first relationship between a user attribute entity and an exercise category entity, and a second relationship between an exercise category entity and a disease type entity, and,
  wherein said querying the exercise knowledge graph according to each query statement in the at least one query statement respectively to obtain the target exercise mode list and the evaluation attribute list corresponding to the target exercise mode list comprises:
  in response to the physical activity level assessment result of the user being a high level, querying the first relationship and the second relationship in the exercise knowledge graph according to the first query statement to obtain the target exercise mode list;
  in response to the physical activity level assessment result of the user being a medium level or below, querying the first relationship and the second relationship in the exercise knowledge graph according to the first query statement to obtain an initial exercise mode list, and querying the exercise knowledge graph according to the second query statement to obtain exercise modes that satisfy the physical activity level assessment result of the user in the initial exercise mode list as the target exercise mode list;
  acquiring the evaluation attribute list corresponding to the target exercise mode list.

In some embodiments, said determining at least one exercise program according to the target exercise mode list and the evaluation attribute list comprises:
  acquiring a target calorie consumption of the user;
  combining the exercise modes comprised in the target exercise mode list to obtain an exercise combination result, the exercise combination result comprising at least one exercise mode;
  extracting an evaluation attribute in the evaluation attribute list corresponding to the exercise combination result according to the exercise combination result;
  determining a recommended time combination corresponding to the exercise combination result according to the evaluation attribute corresponding to the exercise combination result and the target calorie consumption, the recommended time combination comprising a recommended exercise duration corresponding to each exercise mode in the exercise combination result;

combining the exercise combination result with the recommended time combination corresponding to the exercise combination result as the at least one exercise program.

In some embodiments, each evaluation attribute comprises a per unit calorie consumption corresponding to a respective exercise mode, and said determining a recommended time combination corresponding to the exercise combination result according to the evaluation attribute corresponding to the exercise combination result and the target calorie consumption comprises:

determining the recommended time combination corresponding to the exercise combination result according to a sum of products of per unit calorie consumption corresponding to exercise modes comprised in the exercise combination result and respective recommended exercise durations being equal to the corresponding target calorie consumption.

In some embodiments, said determining at least one exercise program according to the target exercise mode list and the evaluation attribute list comprises:

acquiring an exercise frequency of the user during an exercise planning period;

combining the exercise modes comprised in the target exercise mode list to obtain an exercise combination result, the exercise combination result comprising at least one exercise mode;

determining a maximum activity amount and a minimum activity amount to which the exercise planning period corresponds;

determining a time array according to the maximum activity amount and the minimum activity amount, the time array comprising the exercise frequency and a recommended exercise duration corresponding to the exercise frequency;

allocating the time array to the exercise combination result according to the exercise frequency in the exercise planning period to obtain the at least one exercise program.

In some embodiments, said combining the exercise modes comprised in the target exercise mode list to obtain an exercise combination result comprises:

according to a physical activity level assessment result of the user, acquiring a preset number of exercise modes corresponding to the physical activity level assessment result of the user from the exercise modes comprised in the target exercise mode list as the exercise combination result.

In some embodiments, the evaluation attribute list comprises a plurality of evaluation attributes corresponding to the exercise modes, and said performing ranking processing on the at least one exercise program according to the evaluation attribute list comprises:

determining an exercise risk level of the user according to the basic information of the user;

ranking the at least one exercise program according to the plurality of evaluation attributes and the exercise risk level.

In some embodiments, said ranking the at least one exercise program according to the plurality of evaluation attributes and the exercise risk level comprises:

acquiring a weight coefficient corresponding to each evaluation attribute in the plurality of evaluation attributes of each exercise mode;

calculating a weighted sum based on weight coefficients corresponding to the plurality of evaluation attributes and values corresponding to the plurality of evaluation attributes to obtain a first multiplication result;

multiplying a value of the exercise risk level corresponding to said each exercise mode by a weight coefficient corresponding to the exercise risk level to obtain a second multiplication result;

taking a sum of the first multiplication result and the second multiplication result as an evaluation index of said each exercise mode in the at least one exercise program;

determining a comprehensive evaluation index of each exercise program according to the evaluation index for each exercise mode and a weight coefficient corresponding to each exercise mode;

ranking the at least one exercise program according to the comprehensive evaluation index of each exercise program.

In some embodiments, said ranking the at least one exercise program according to the plurality of evaluation attributes and the exercise risk level comprises:

acquiring a weight coefficient corresponding to each evaluation attribute in the plurality of evaluation attributes of each exercise mode;

calculating a weighted sum based on weight coefficients corresponding to the plurality of evaluation attributes and values corresponding to the plurality of evaluation attributes to obtain a first multiplication result;

multiplying a value of the exercise risk level corresponding to said each exercise mode by a weight coefficient corresponding to the exercise risk level to obtain a second multiplication result multiplying a recommended exercise duration of said each exercise mode by a weight coefficient corresponding to the recommended exercise duration to obtain a third multiplication result;

taking a sum of the first multiplication result, the second multiplication result, and the third multiplication result as an evaluation index of said each exercise mode in the at least one exercise program;

determining a comprehensive evaluation index of each exercise program according to the evaluation index of each exercise mode and a weight coefficient corresponding to each exercise mode;

ranking the at least one exercise program according to the comprehensive evaluation index of each exercise program.

In some embodiments, prior to said querying a pre-established exercise knowledge graph according to the basic information of the user, the method further comprises:

determining an exercise risk level of the user according to the basic information of the user;

determining a range of exercise modes comprised in the target exercise mode list according to the exercise risk level.

In some embodiments, said determining an exercise risk level of the user according to the basic information of the user comprises:

inputting the basic information of the user into a pre-established exercise risk classification model to obtain the exercise risk level of the user.

In some embodiments, the basic information of the user comprises a target disease type, a target user attribute and a physical activity level assessment result of the user, and wherein said acquiring the basic information of the user comprises:

acquiring the target disease type, the target user attribute and the physical activity level assessment result of the user in an electronic questionnaire manner.

In some embodiments, the basic information of the user comprises a target disease type, a target user attribute and a physical activity level assessment result of the user, and
wherein said acquiring the basic information of the user comprises:
acquiring the target disease type and the target user attribute of the user through user physical examination data;
acquiring the physical activity level assessment result of the user in an electronic questionnaire manner.

In some embodiments, the electronic questionnaire manner comprises at least one of a human-computer interaction presentation interface and a voice conversation mode.

Some embodiments of the present disclosure further provide an exercise recommendation apparatus, comprising:
an information acquirer configured to acquire basic information of a user;
a graph querier configured to query a pre-established exercise knowledge graph according to the basic information of the user to obtain a target exercise mode list comprising exercise modes, and an evaluation attribute list comprising evaluation attributes corresponding to the target exercise mode list, each evaluation attribute indicating an attribute index for evaluating a corresponding exercise mode;
a program determiner configured to determine at least one exercise program according to the target exercise mode list and the evaluation attribute list, each exercise program in the at least one exercise program comprising at least one exercise mode and a recommended exercise duration corresponding to the at least one exercise mode;
a program ranker configured to rank the at least one exercise program according to the evaluation attribute list to obtain a ranking result;
a program recommender configured to recommend at least one target exercise program according to the ranking result.

Some embodiments of the present disclosure provide an electronic device comprising a memory, a processor, and computer instructions stored on the memory and executable on the processor, implementing the method described according to an embodiment of the present disclosure when the computer instructions are executed by the processor.

In some embodiments, the electronic device further comprises: an input device and an output device;
the input device being configured to acquire basic information of a user;
the output device being configured to recommend at least one exercise program to the user.

Some embodiments of the present disclosure provide a non-transitory computer-readable storage medium having computer instructions stored thereon, which is configured to implement the method described according to an embodiment of the present disclosure when the computer instructions are executed.

BRIEF DESCRIPTION OF THE DRAWINGS

By reading the detailed description of the non-limiting embodiments with reference to the following drawings, other features, purposes and advantages of the present disclosure will become more apparent:

FIG. 11 illustrates a schematic view of a questionnaire data collection form according to an embodiment of the present disclosure;

FIG. 12 illustrates a schematic view of a query interface according to an embodiment of the present disclosure;

FIG. 13 illustrates a schematic view of a calorie calculation interface according to an embodiment of the present disclosure;

FIG. 14 illustrates a schematic view of an information collection interface according to an embodiment of the present disclosure;

FIG. 15 illustrates a schematic view of an exercise program presentation interface according to an embodiment of the present disclosure;

FIG. 16 illustrates a schematic view of a weekly exercise plan presentation interface according to an embodiment of the present disclosure;

DETAILED DESCRIPTION

Figure 1:
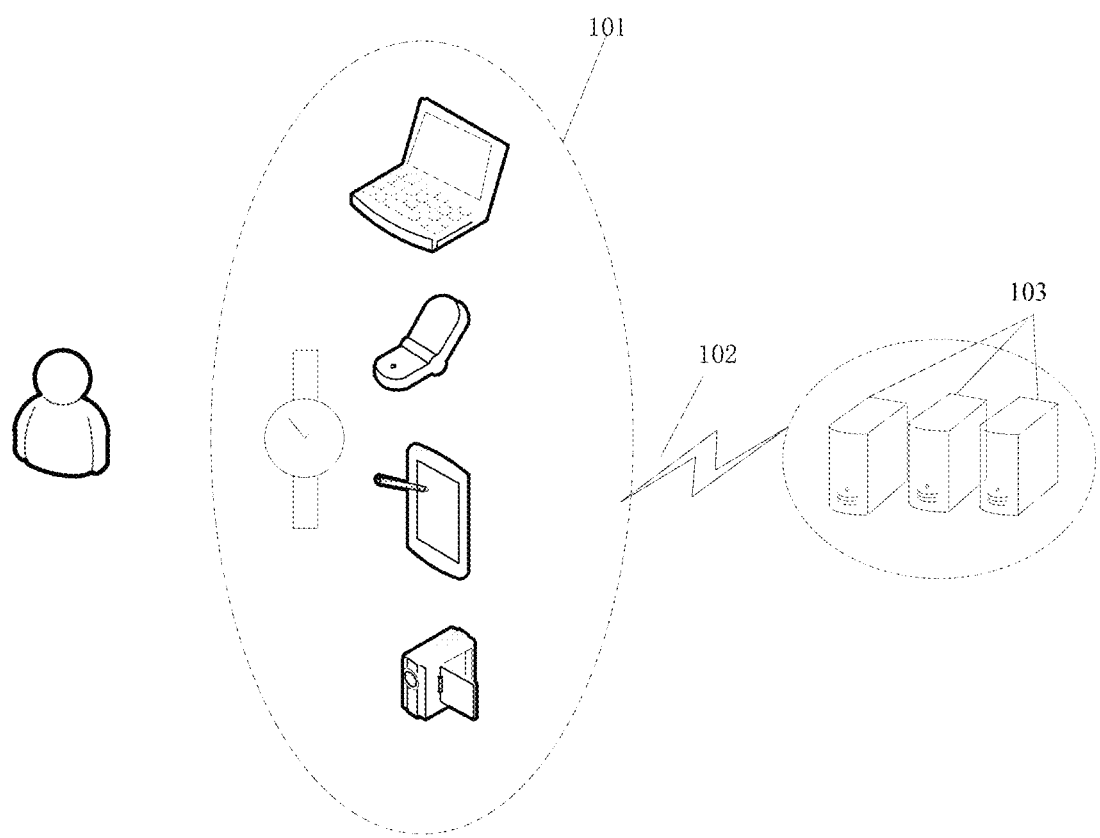
FIG. 1 illustrates a schematic view of an application scenario of an exercise recommendation method according to an embodiment of the present disclosure.

The present disclosure will be further described in detail below with reference to the accompanying drawings and embodiments. It can be understood that the specific embodiments described here are only used to explain the relevant disclosure, but not to limit the disclosure. In addition, it is to be further noted that, to facilitate description, only the parts related to the disclosure are shown in the drawings.

It is to be noted that the embodiments in the present disclosure and the features in the embodiments can be combined with each other in the case of causing no conflict. Hereinafter, the present disclosure will be described in detail with reference to the drawings and in conjunction with the embodiments.

Referring to FIG. 1, FIG. 1 illustrates a schematic view of an application scenario of an exercise recommendation method according to an embodiment of the present disclosure.

As shown in FIG. 1, the user may use a terminal device 101 to query an exercise recommendation result suitable for himself. The user may obtain the exercise recommendation result through an exercise recommendation application pre-installed in the terminal device. The exercise recommendation application may be implemented as a client mode or via a web page mode. After acquiring query conditions input by the user, the terminal device 101 sends the query conditions to a server 103 via a network 102. The query conditions may include, but are not limited to, the user physical examination data, the basic information input by the user, the physical activity level provided by the user through a human-computer interaction interface, and so on.

The above terminal device 101 may be a mobile device such as a smart phone, a tablet computer, smart glasses, a smart watch, other wearable devices, or an electronic device such as a desktop computer, but is not limited thereto. For example, the exercise recommendation method provided in an embodiment of the present disclosure may also be executed on the terminal device 101. For example, the exercise recommendation method provided in an embodiment of the present disclosure may be partially executed on the terminal device 101, and partially sent to the server 103 to be executed, that is, it is executed by the terminal device 101 and the server 103 cooperatively.

The server 103 executes a query program according to the query conditions sent by the terminal device 101 to seek exercise recommendation results related to the query conditions. The aforementioned server 103 may be an independent physical server, may also be a server cluster or a distributed system composed of multiple physical servers, and may further be a cloud server that provides cloud services, cloud databases, cloud computing, cloud functions, cloud storage, network services, cloud communications, middleware services, domain name services, security services, CDN, and basic cloud computing services such as big data and artificial intelligence platforms.

The above network 102 includes, but is not limited to, a wireless network or a wired network, and the wireless network or the wired network uses standard communication technologies and/or protocols. The network is usually the Internet, and may also be any network, including but not limited to a local area network (LAN), a metropolitan area network (MAN), a wide area network (WAN), a mobile, wired or wireless network, a private network, a virtual private network, or any combination thereof.

In the related art, the exercise mode is recommended to the user according to the fitness demand data of the user, but the user's own actual physical condition is not taken into account, for example, the user may suffer from a chronic disease. For patients with chronic diseases, proper exercises have a positive effect on chronic diseases and help to improve glucose metabolism. For another example, for patients with certain diseases, there are contraindicated exercise modes. For example, patients with epilepsy need to avoid skiing, diving and other dangerous exercises. The user's own actual physical condition is not taken into account in the related art, which results in limitations in the exercise recommendation scheme.

The present disclosure proposes a technical solution of an exercise recommendation method, which takes the relationship between the exercise amount and the disease characteristics into consideration in a comprehensive manner, and effectively improves the accuracy of the exercise recommendation result.

Figure 2:
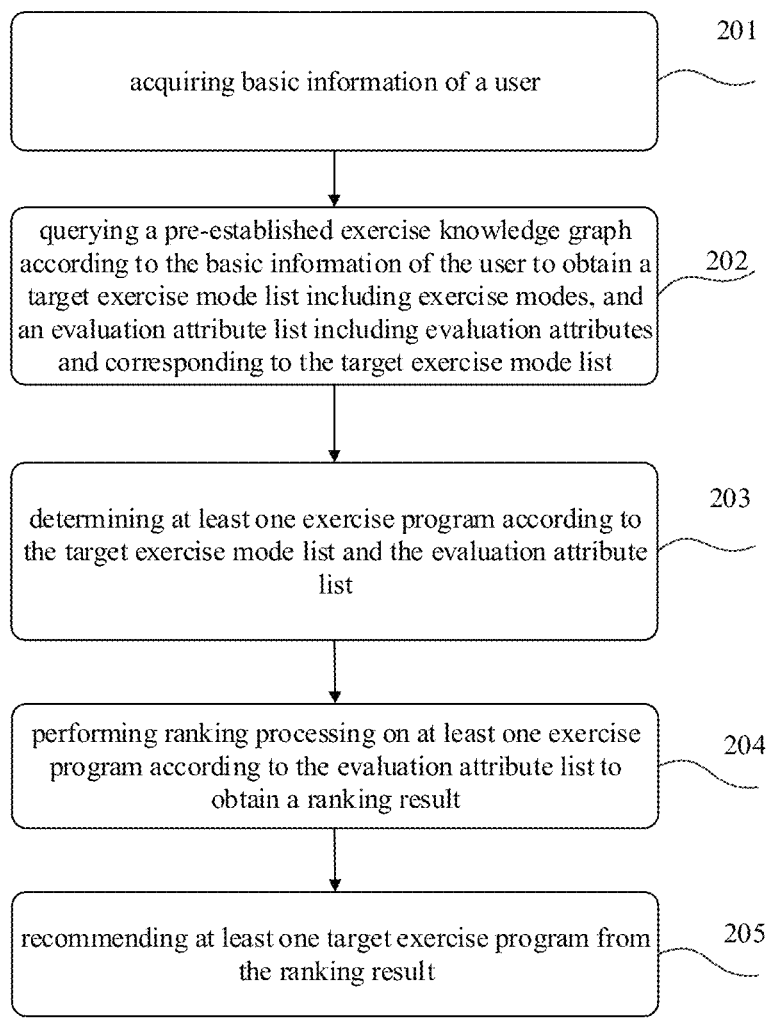
FIG. 2 illustrates a flow chart of an exercise recommendation method according to an embodiment of the present disclosure.

Referring to FIG. 2, FIG. 2 illustrates a flow chart of an exercise recommendation method according to an embodiment of the present disclosure. As shown in FIG. 2, the method may be executed by an exercise recommendation apparatus, and the exercise recommendation apparatus may be configured in a terminal device or a server. The method comprises step 201-205.

Step 201: Acquire basic information of a user.

For example, the basic information of the user comprises a target disease type of the user, a target user attribute of the user, and a physical activity level assessment result of the user.

The aforementioned target disease type refers to disease keywords corresponding to the user's own condition, which is, for example, extracted from the user physical examination data. For example, the disease keywords include but are not limited to fasting blood glucose, postprandial blood glucose, fat content in the liver, fatty liver, dyslipidemia, diabetes, etc. Extraction methods include but are not limited to a TF-IDF (Term Frequency-Inverse Document Frequency) algorithm, a TextRank algorithm, a word2vec algorithm, a Bert pre-training model-based BiLSTM-CRF (Bi-directional Long Short-Term Memory-Conditional Random Fields) algorithm, etc. For example, according to the Bert pre-training model-based BILSTM-CRF algorithm, multiple disease keywords are extracted from the user physical examination data, indicating the user suffering from fatty liver, diabetes, etc. When the physical examination data is structured data (for example, structured data stored in a key-value format), the disease keywords can be directly obtained by reading value corresponding to key. For example, the physical examination report shows "current medical history (i.e. key): hypertension (i.e. value)". When the physical examination data is unstructured data, the disease keywords can be extracted using a keyword extraction algorithm. For example, the physical examination report shows "past history: hypertension history for more than 10 years, not taking antihypertensive drugs, self-reporting normal blood pressure, not regularly monitoring blood pressure changes", and the disease keywords extracted by a keyword extraction algorithm are: hypertension, duration: more than 10 years. The aforementioned target disease type may also be input by the user through an interactive interface, for example.

The aforementioned target user attribute refers to user personal information. The user personal information includes but is not limited to the gender, age, height, weight, etc. of the user. For example, the user personal information may be obtained from the physical examination data, or input through an interactive interface.

The aforementioned physical activity level assessment result is a grade index for evaluating the user's physical fitness. The physical activity level assessment result may be fed back to the user in the form of a text assessment report or a voice assessment report. The report contents may include the current activity level, the activity frequency, the activity intensity, the sitting time, the exercise safety level, and a current activity level comparison chart with other populations (such as populations with indexes such as the same age, gender, occupation, etc.). The above physical activity level assessment result includes, but is not limited to, high level, medium level, and low level. The high level means adequate physical activity, the medium level means average physical activity, and the low level means inadequate physical activity.

In some embodiments, at the time of acquiring the basic information of the user, it is possible to acquire the target disease type, the target user attribute, and the physical activity level assessment result of the user in an electronic questionnaire manner, and it is also possible to acquire the target disease type of the user and the target user attribute through the user physical examination data, and acquire the physical activity level assessment result of the user in an electronic questionnaire manner.

In some embodiments, it is also possible to acquire the user physical examination data, then determine the electronic questionnaire content provided to the user according to the user physical examination data, and acquire the physical activity level assessment result of the user according to the electronic questionnaire content.

The user physical examination data may be a comprehensive assessment result of the user physical examination result. For example, the comprehensive assessment result indicates that the user is in a healthy state, or the user is in a sub-healthy state, or the user suffers from a chronic disease.

The above electronic questionnaire manner includes, but is not limited to, a human-computer interaction presentation interface or a voice conversation.

Said determining the electronic questionnaire content provided to the user according to the user physical examination data comprises: when the user physical examination data indicates that the user is in a healthy state, providing the user with the international physical activity questionnaire content; when the user physical examination data indicates that the user is in a sub-healthy state or the user suffers from a chronic disease or other diseases, providing the user with a pre-activity readiness questionnaire.

The international physical activity questionnaire (IPAQ) can collect the user's exercise frequencies and exercise durations of different exercise intensities in the last week. The physical activity level assessment results of the user may be classified into three types: low level (i.e. inadequate physical activity level), medium level (average physical activity level), and high level (adequate physical activity level).

For a user with sub-health, chronic diseases or other diseases, the physical activity level assessment result of the user may be acquired through the pre-activity readiness questionnaire (PAR-Q), which is used as an evaluation parameter for the safety of the user's exercise.

As shown in FIG. 11, the IPAQ and PAR-Q questionnaire contents may be provided to the user via a human-computer interaction presentation interface, so that the basic information of the user can be obtained through the above electronic questionnaire contents filled out by the user. The above IPAQ and PAR-Q questionnaire contents may also be provided to the user in a voice conversation manner, so as to extract the basic information of the user through the voice conversation of the user.

The embodiment of the present disclosure can improve the satisfaction degrees of different users in using the product through a variety of electronic questionnaire manners. For example, the voice conversation manner can provide the elderly people with convenient operation modes, thereby improving the satisfaction degree of elderly users in using the product.

Step 202: Query a pre-established exercise knowledge graph according to the basic information of the user to obtain a target exercise mode list including exercise modes, and an evaluation attribute list including evaluation attributes corresponding to the target exercise mode list, each of the evaluation attributes indicating an attribute index for evaluating a corresponding exercise mode.

The above target exercise mode list includes one or more exercise modes. Each exercise mode is obtained by querying a pre-established exercise knowledge graph based on the basic information of the user.

The above evaluation attribute list includes one or more evaluation attributes. The evaluation attribute refers to an attribute index for evaluating the exercise mode. The evaluation attributes include but are not limited to: exercise intensity value, whether it is a common exercise, whether equipment is required, exercise difficulty, per unit calorie consumption, etc.

For example, the target exercise mode list includes {"brisk walking", "medical gymnastics", "Tai Chi", "Ba Duan Jin", "running", "square dance", "playing badminton", "aerobics"}.

The evaluation attribute list corresponding to the above target exercise mode list may include {[exercise intensity value, whether it is a common exercise, whether equipment is required, exercise difficulty, per unit calorie consumption]$_{brisk\ walking}$; [exercise intensity value, whether it is a common exercise, whether equipment is required, exercise difficulty, per unit calorie consumption]$_{medical\ gymnastics}$; [exercise intensity value, whether it is a common exercise, whether equipment is required, exercise difficulty, per unit calorie consumption]$_{Tai\ chi}$; [exercise intensity value, whether it is a common exercise, whether equipment is required, exercise difficulty, per unit calorie consumption]$_{Ba\ Duan\ Jin}$; [exercise intensity value, whether it is a common exercise, whether equipment is required, exercise difficulty, per unit calorie consumption]$_{running}$; [exercise intensity value, whether it is a common exercise, whether equipment is required, exercise difficulty, per unit calorie consumption]$_{square\ dance}$; [exercise intensity value, whether it is a common exercise, whether equipment is required, exercise difficulty, per unit calorie consumption]$_{playing\ badminton}$; [exercise intensity value, whether it is a common exercise, whether equipment is required, exercise difficulty, per unit calorie consumption]$_{aerobics}$}.

It is to be noted that the above exercise modes include but are not limited to brisk walking, running, swimming, Tai Chi, push-ups, medical gymnastics, Ba Duan Jin, square dance, playing badminton, aerobics, basketball, etc.

Querying a pre-established exercise knowledge graph according to the basic information of the user to obtain a target exercise mode list including exercise modes and an evaluation attribute list including evaluation attributes corresponding to the target exercise mode list comprises:

creating at least one query statement according to the basic information of the user;

querying the exercise knowledge graph according to each query statement in the at least one query statement respectively to obtain an exercise mode list and an evaluation attribute list corresponding to the exercise mode list.

Creating at least one query statement according to the basic information of the user may comprise:

acquiring a physical activity level assessment result of the user;

in response to the physical activity level assessment result of the user being a high level, creating a first query statement using the target user attribute and the target disease type as query conditions;

in response to the physical activity level assessment result of the user being a medium level or below, creating a first query statement using the target user attribute and the target disease type as query conditions, and creating a second query statement using the physical activity level assessment result of the user as a query condition.

In the embodiment provided by the present disclosure, when the physical activity level assessment result is a medium level or below, the execution order of creating the first query statement and creating the second query statement may not be limited. For example, the second query statement may be created based on the first query statement, that is, the physical activity level assessment result of the user is added to the query conditions of the first query statement to create the second query statement.

In some embodiments, the pre-established exercise knowledge graph includes a first relationship between a user attribute entity and an exercise category entity, and a second relationship between an exercise category entity and a disease type entity. Therefore, at the time of querying the exercise knowledge graph according to each query statement in the at least one query statement respectively to obtain the target exercise mode list and the evaluation attribute list corresponding to the target exercise mode list, it is possible to query the first relationship and the second relationship in the exercise knowledge graph according to the first query statement in response to the physical activity level assessment result of the user being a high level to obtain the target exercise mode list; it is also possible to query the first relationship and the second relationship in the exercise knowledge graph according to the first query statement in response to the physical activity level assessment result of the user being a medium level or below to obtain an initial exercise mode list, and query the exercise knowledge graph according to the second query statement to obtain exercise modes in the initial exercise mode list that satisfy the physical activity level assessment result of the user as the target exercise mode list; finally, the evaluation attribute list corresponding to the target exercise mode list can be obtained.

Step 203: Determine at least one exercise program according to the target exercise mode list and the evaluation attribute list, each exercise program in the at least one exercise program comprising at least one exercise mode and a recommended exercise duration corresponding to the at least one exercise mode.

In some embodiments, at least one exercise program may be determined according to the target exercise mode list, the evaluation attribute list, and the target calorie consumption of the user. In some embodiments, at least one exercise program may also be determined according to the target exercise mode list, the evaluation attribute list, and the exercise planning period of the user.

The above target calorie consumption refers to the target calories that the user desires or needs to consume. The target calorie consumption may be input by the user at the human-computer interaction interface, and may also be determined from the daily food intake input by the user at the human-computer interaction interface.

The above exercise program refers to a combination of an exercise mode and a recommended exercise duration corresponding to the exercise mode. For example, the exercise programs are ["brisk walking", 35], ["Tai Chi", 45], etc., where 35 and 45 indicate that the recommended exercise duration corresponding to brisk walking is 35 minutes, and the recommended exercise duration corresponding to Tai Chi is 45 minutes.

When determining an exercise program according to the target calorie consumption, one or more exercise programs can be determined by means of the target exercise mode list, a per unit calorie consumption in the evaluation attribute list corresponding to a respective exercise mode and the target calorie consumption of the user.

When determining an exercise program according to the exercise planning period of the user, one or more exercise programs can be determined by means of the target exercise mode list, the evaluation attribute list, and the exercise planning period. The exercise planning period refers to the length of time for which the user plans to exercise. For example, the length of the exercise planning period is one week, which means that the length of time for which the user plans to exercise is 7 days. The setting of the exercise planning period may be input by a third party at the human-computer interaction interface. The third party includes but is not limited to the user, and the exercise planning period may also be a default recommended value.

Step 204: Perform ranking processing on at least one exercise program according to the evaluation attribute list to obtain a ranking result.

After one or more exercise programs are obtained, the exercise programs are ranked by means of the evaluation attribute list. For example, the exercise programs may be ranked by means of a combination result of part of the evaluation attributes in the evaluation attribute list to obtain a ranking result. The ranking scheme may be in an ascending order or a descending order.

Step 205: Recommend at least one target exercise program from the ranking result.

Part of the exercise programs are recommended from the above ranking result as an exercise recommendation result, i.e. target exercise programs. For example, after evaluating each exercise program according to the evaluation attributes, the top N exercise programs from a plurality of exercise programs whose evaluation results are arranged in a descending order (i.e. the evaluation results are arranged from high to low) are determined as a recommendation result. The value range of N may be determined according to the user grade or the physical activity level assessment result of the user. When the physical activity level assessment result indicates a high level, N may be taken as 3. When the physical activity level assessment result indicates a medium level, N may be taken as 2. When the physical activity level assessment result indicates a low level, N may be taken as 1 or 0. When N is zero, the user is prompted not to take exercise.

In some embodiments, the embodiment of the present disclosure may also determine an exercise risk level of the user according to the basic information of the user prior to querying a pre-established exercise knowledge graph according to the basic information of the user, and determine the range of exercise modes, i.e. the range of recommended exercise modes, included in the target exercise mode list according to the exercise risk level. For example, if the exercise risk level is high, no exercise mode is recommended to the user. Or, when the exercise risk level is medium, at least one of aerobic exercise, strength exercise, and flexible exercise is recommended to the user.

In the embodiment of the present disclosure, a pre-established exercise knowledge graph is queried according to the basic information of the user to obtain a target exercise mode list, and an evaluation attribute list corresponding to the target exercise mode list, then at least one exercise program is determined according to the target exercise mode list, the evaluation attribute list and the target calorie consumption, and finally an exercise recommendation result (i.e. target exercise program) is obtained from the at least one exercise program that has been ranked. Compared with the related art, different exercise programs can be recommended for each user, which effectively improves the accuracy of exercise recommendation.

Figure 3:
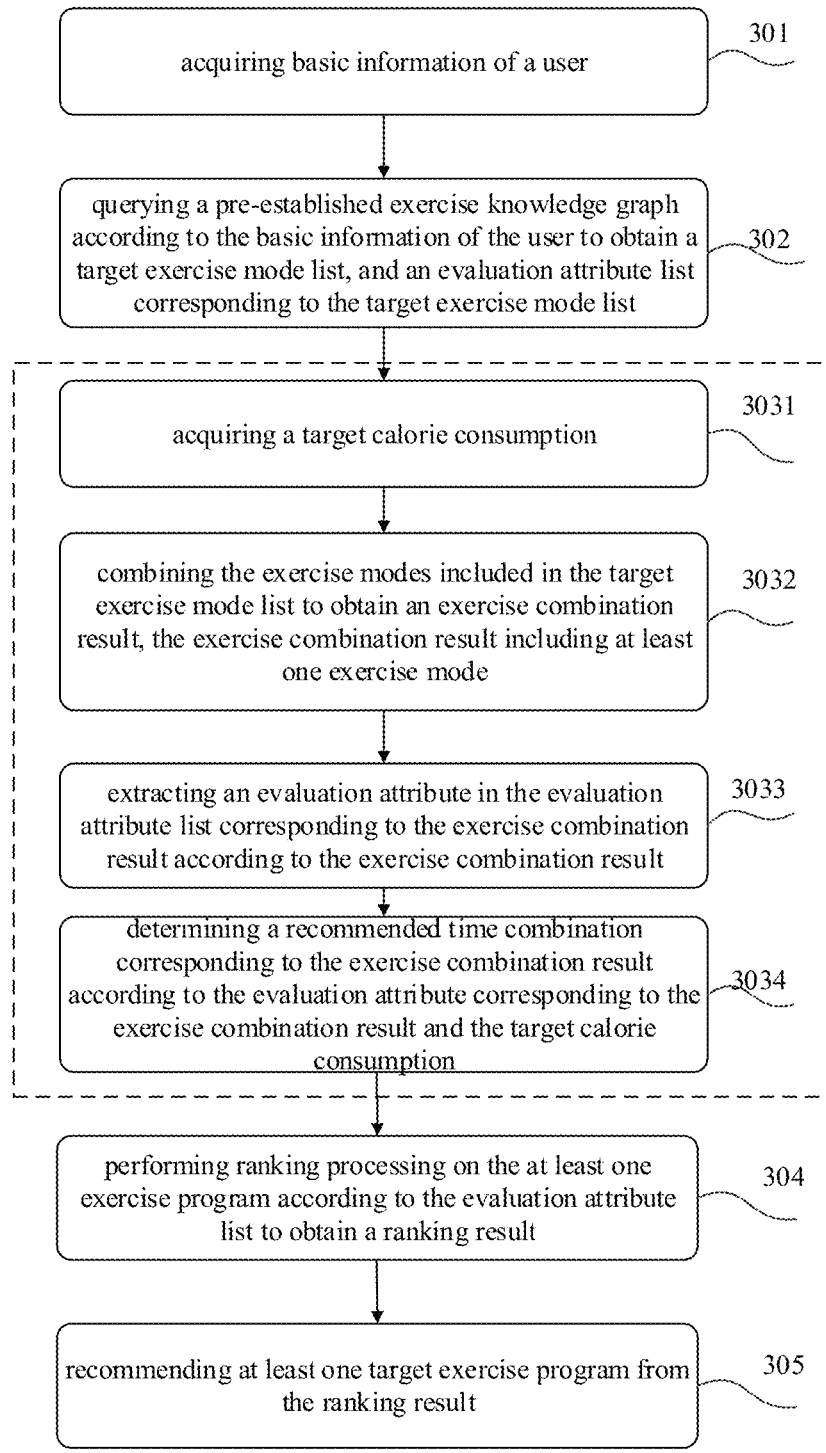
FIG. 3 illustrates a flow chart of another exercise recommendation method according to an embodiment of the present disclosure.

Some embodiments of the present disclosure provide an exercise recommendation method. Referring to FIG. 3, FIG. 3 illustrates a flow chart of another exercise recommendation method according to an embodiment of the present disclosure. The method may be executed by an exercise recommendation apparatus, and the exercise recommendation apparatus may be configured in a terminal device or a server. The method comprises the following steps.

Step 301: Acquire basic information of a user.

After acquiring the basic information of the user, the basic information of the user is preprocessed, for example, discretizing the input characteristics of the physical examination data of the user:

Gender: male, female;
Population division: teenagers (12~17 years old), adults (18~64 years old), elderly people (over 65 years old);
Women's special physiological conditions: menstrual period, pregnancy, postpartum period, menopause;
Physical condition: unknown, thin, normal, overweight, obesity, central obesity, pre-central obesity;
Physical activity level: unknown, low, medium, high;
Fitness environment: unknown, gym, family, bare hands;
Health status: unknown, healthy, sub-healthy, hypertension, diabetes, osteoporosis, hyperlipidemia, etc.;
Fitness goals: unlimited, fat loss, shaping, muscle gain, strength, lowering blood glucose, regulating blood pressure, improving blood lipid, etc.;
Health status: healthy people, sub-healthy people, people with chronic diseases, people with limited physical activity, people with developmental disabilities, people with other diseases;
Types of exercise: aerobic exercise, strength exercise, stretching exercise, balance exercise, flexibility training;
Exercise intensity: low intensity, medium intensity, high intensity, medium-low intensity, medium-high intensity;
Difficulty degree: low, medium, high;
Exercise heart rate: performing calculation using a maximum heart rate method and a heart rate reserve method;
Human resting energy consumption: performing calculation using the Mifflin-St Jeor formula based on gender, height, weight and age, the unit being "kcal/day".

The user characteristics are discretized, for example, there are three categories of age, and those who do not meet these ages cannot be recommended exercise programs. Then, each characteristic of the user is represented as a low-dimensional embedding vector, wherein the embedding vector can be obtained, for example, through a pre-trained WORD2VEC model, and the training data used for training comes from medical websites and data compiled in sports medicine books.

Step 302: Query a pre-established exercise knowledge graph according to the basic information of the user to obtain a target exercise mode list including exercise modes, and an evaluation attribute list including evaluation attributes corresponding to the target exercise mode list, each of the evaluation attributes indicating an attribute index for evaluating a corresponding exercise mode.

Next, at least one exercise program is determined according to the target exercise mode list and the evaluation attribute list, and each exercise program in the at least one exercise program comprises at least one exercise mode and a recommended exercise duration corresponding to the at least one exercise mode, which may comprise steps 3031-3034.

Step 3031: Acquire a target calorie consumption of the user;

Step 3032: Combine the exercise modes included in the target exercise mode list to obtain an exercise combination result, where the exercise combination result includes at least one exercise mode;

The above exercise combination result refers to the result of combining one or more exercise modes. Combining the target exercise mode list may comprise:

according to the physical activity level assessment result of the user, acquiring a preset number of exercise modes corresponding to the physical activity level assessment result of the user from the exercise modes included in the target exercise mode list, wherein the preset number corresponding to the physical activity level assessment result of the user is a fixed attribute pre-stored in the exercise knowledge graph.

In some embodiments, after the target exercise mode list is obtained, a preset number of exercise modes corresponding to the physical activity level assessment result of the user can be directly acquired from the exercise modes included in the target exercise mode list according to the physical activity level assessment result of the user as an exercise combination result. Assuming that the target exercise mode list is $\{e_1, e_2, \ldots e_n\}$, the physical activity level assessment result of the user is a medium level, and the preset number corresponding to the physical activity level assessment result of the user is 2, when the exercise combination result is acquired from the target exercise mode list, a first exercise combination result $(e_1, e_2)$ and a second exercise combination result $(e_4, e_6)$ may be obtained. This is only for explanation and does not limit the number of exercise combination results.

When a preset number of exercise modes corresponding to the physical activity level assessment result of the user is acquired from the exercise modes included in the target exercise mode list according to the physical activity level assessment result of the user as an exercise combination result, a plurality of exercise combination results can be obtained. The plurality of exercise combination results are ranked according to the comprehensive evaluation indexes to which the exercise combination results correspond, and one or more target exercise combination results are determined according to the ranking result.

Assuming that the target exercise mode list is $\{e_1, e_2, \ldots e_n\}$, the physical activity level assessment result of the user is a medium level, and the preset number corresponding to the physical activity level assessment result of the user is 2, a plurality of exercise combination results are obtained, such as $(e_1, e_2)$, $(e_4, e_6)$. For each exercise combination result, the comprehensive evaluation index $K_{comprehensive}$ of each exercise combination result is determined by the following comprehensive evaluation index calculation formula:

$$K_{comprehensive}=a_1*K_{exercise\ mode1}+a_2*K_{exercise\ mode2}+\ldots a_N*K_{exercise\ modeN};$$

wherein $a_1, a_2, \ldots, a_N$ represents a weight coefficient corresponding to each exercise mode, and its value is in the range of 0~1. $K_{exercise\ mode1}, \ldots, K_{exercise\ modeN}$ represents an evaluation index of each exercise mode. N is the number of evaluation methods (i.e. the number of exercise modes).

The exercise combination results are then ranked according to the comprehensive evaluation indexes in a descending order or an ascending order to obtain an exercise combination result with the highest comprehensive evaluation index (which may be a few highest-ranked ones) as a target exercise combination result.

Combining the exercise modes included in the target exercise mode list may further comprise:

ranking the exercise modes included in the target exercise mode list according to the evaluation attribute list corresponding to the target exercise mode list to obtain a ranked target exercise mode list;

according to the physical activity level assessment result of the user, acquiring a preset number of exercise modes corresponding to the physical activity level assessment result of the user from the exercise modes included in the ranked target exercise mode list as an exercise combination result.

In the embodiment of the present disclosure, the target exercise mode list may be ranked to improve the accuracy of the recommendation result.

Ranking the exercise modes included in the target exercise mode list may comprise:

calculating an evaluation result of each exercise mode according to the evaluation attribute list to which each exercise mode corresponds; then ranking the exercise modes included in the target exercise mode list according to an evaluation index K.

The evaluation index K to which each exercise mode corresponds is calculated according to the evaluation index formula:

$$K=k_1*\text{exercise intensity value}+k_2*\text{whether it is a common exercise}+k_3*\text{whether equipment is required}+k_4*\text{exercise difficulty}+k_5*\text{exercise risk level};$$

wherein $k_1$ to $k_5$ are the weight coefficients corresponding to the exercise intensity value, whether it is a common exercise, whether exercise equipment is required, the exercise difficulty, and the exercise risk level, respectively.

Assuming that the ranked target exercise mode list is $\{e_3, e_1, \ldots e_n, \ldots e_2\}$, the exercise mode(s) is acquired according to the preset number corresponding to the physical activity level assessment result of the user. For example, when the physical activity level assessment result of the user is a high level, the three highest-ranked exercise modes may be acquired from the ranked target exercise mode list as an exercise combination result, for example, $(e_3, e_1, e_4)$.

For another example, when the physical activity level assessment result of the user is a medium level, the two highest-ranked exercise modes may be obtained from the ranked target exercise mode list as an exercise combination result $(e_3, e_1)$.

Step 3033: Extract an evaluation attribute in the evaluation attribute list corresponding to the exercise combination result according to the exercise combination result.

Step 3034: Determine a recommended time combination corresponding to the exercise combination result according to the evaluation attribute corresponding to the exercise combination result and the target calorie consumption, the recommended time combination including a recommended exercise duration corresponding to each exercise mode in the exercise combination result.

The evaluation attribute corresponding to the above exercise combination result refers to an evaluation attribute corresponding to each exercise mode in the exercise combination result. After the exercise combination result is obtained, recommended exercise durations corresponding to the exercise modes may be allocated to the exercise modes included in the exercise combination result according to the target calorie consumption or the exercise planning period.

When recommended exercise durations corresponding to the exercise modes are allocated according to the target calorie consumption, assuming that the exercise combination result is $(e_3, e_1)$, extracting an evaluation attribute corresponding to the exercise combination result from the evaluation attribute list according to the exercise combination result means extracting ([per unit calorie consumption] $e_3$, [per unit calorie consumption]$e_1$) from the evaluation attribute list.

Then, determining a recommended time combination corresponding to the exercise combination result according to the evaluation attribute corresponding to the exercise combination result and the target calorie consumption may comprise: according to the sum of the products of the per unit calorie consumptions corresponding to the exercise modes included in the exercise combination result and the respective recommended exercise durations being equal to the corresponding target calorie consumption, determining a recommended time combination corresponding to the exercise combination result.

The recommended time combination corresponding to the exercise combination result is determined according to the following recommended time formula:

$$y=c_1*t_1+c_2*t_2+L+c_n*t_n$$

y represents the target calorie consumption; n represents the number of exercise modes included in the exercise combination vector; $c_i$ represents the per unit calorie consumption corresponding to the i-th exercise mode; $t_i$ represents the recommended exercise duration corresponding to the i-th exercise mode.

For example, according to the above recommended time formula, the target calorie consumption y being 340 kcal is taken as a restrictive condition, and the exercise combination result $(e_3, e_1)$ corresponds to the per unit calorie consumption $(c_{e3}, c_{e1})$, thus it can be determined that the recommended exercise duration corresponding to each exercise mode in the exercise combination result $(e_3, e_1)$ is $[(e_3,30), (e_1,50)]$. That is, when the target calorie consumption is 340 kcal, the per unit calorie consumption $(c_{e3}, c_{e1})$ is substituted into the above recommended time formula, and it can be obtained that the recommended exercise duration corresponding to the exercise mode $e_3$ is 30 minutes, and the recommended exercise duration corresponding to the exercise mode $e_1$ is 50 minutes.

The recommended exercise durations corresponding to the exercise modes are then adjusted in combination with the above recommended time formula according to a preset exercise time step (for example, a time interval of 5 minutes), and a plurality of exercise programs to be ranked can be obtained, which may also be called candidate programs or a set of candidates.

The above exercise time step refers to a time interval between two recommended exercise durations of the same exercise mode. For example, if the exercise mode is "brisk walking", the first recommended exercise duration is 30 minutes, and the second recommended exercise duration is 35 minutes, the exercise time step is thus 5 minutes. The exercise time step may be adjusted according to the user's demand. The exercise time step may also be determined according to the basic information of the user. For example, when the basic information of the user indicates that the user is an elderly person, the exercise time step corresponding to an elderly person is 5 minutes, that is, recommended exercise durations suitable for an elderly person are acquired according to a time interval of 5 minutes. When the basic information of the user indicates that the user is a young person, the exercise time step of a young person may be 10 minutes, that is, recommended exercise durations suitable for a young person are acquired according to a time interval of 10 minutes.

For example, in the case of $e_3$="brisk walking" and $e_1$="Tai Chi", the per unit calorie consumption corresponding to "brisk walking" is $c_1$="228 kcal/hour", and the per unit calorie consumption corresponding to "Tai Chi" is $c_2$="240 kcal/hour", according to the above recommended time formula, n=2, y=340, then:

$$c_1 * t_1 + c_2 * t_2 = 340$$

it can be obtained that:

$$(228/60) * t_1 + (240/60) * t_2 = 340$$

That is: $3.8 t_1 + 4 t_2 = 340$ wherein the regular exercise time value range is [10, 15, 20, ..., 85, 90].

For young and middle-aged people, the exercise time t takes a value in [10, 15, 20, ..., 85, 90], and for elderly people, the exercise time t takes a value in [10, 15, ..., 60]. The exercise time steps for young and middle-aged people and elderly people may both be 5 minutes. Under the condition that the target calorie consumption is 340 kcal, it is supposed that $t_1$ takes 10 minutes and $t_2$ takes 75 minutes. Since the basic information of the user indicates that the user is an elderly person, the case in which $t_1$ takes 10 minutes and $t_2$ takes 75 minutes is not suitable for the user. The values of $t_1$ and $t_2$ are adjusted according to the exercise time step. It is supposed that $t_1$ takes 15 minutes and $t_2$ takes 70 minutes, which is also not suitable for the user. The values are discarded until $t_1$ takes 30 minutes and $t_2$ takes 50 minutes. Thus, $t_1$=30 and $t_2$=50 are used as a recommended time combination corresponding to the exercise combination result. In the same way, it is possible to use $t_1$=35 and $t_2$=50 as a recommended time combination corresponding to the exercise combination result, and then use $t_1$=40 and $t_2$=45 as a recommended time combination corresponding to the exercise combination result successively until all combinations that satisfy the target calorie consumption are found in [10, 15, ..., 60].

According to the above recommended time formula, a plurality of exercise programs can be obtained, such as $\{[(e_3,30), (e_1,50)], [(e_3,40), (e_1,45)], [(e_3,50), (e_1,40)]\}$, and the exercise modes included in these exercise programs are the same, all of which are ($e_3$, $e_1$). The recommended exercise durations corresponding to the exercise modes ($e_3$, $e_1$) are different in each exercise program. For example, in the first exercise program $[(e_3,30), (e_1,50)]$, the recommended exercise durations to which the exercise modes ($e_3$, $e_1$) correspond respectively are 30 and 50 minutes. In the second exercise program $[(e_3,40), (e_1,45)]$, the recommended exercise durations to which the exercise modes ($e_3$, $e_1$) correspond respectively are 40 and 45 minutes.

Determining an exercise program according to the target exercise mode list, the evaluation attribute list and the target calorie consumption may result in a set of exercise programs $\{[(e_3,30), (e_1,50)], [(e_3,40), (e_1,45)], [(e_3,50), (e_1,40)]\}$, wherein $[(e_3,30), (e_1,50)]$ represents an exercise program.

Step 304: Perform ranking processing on the at least one exercise program according to the evaluation attribute list to obtain a ranking result.

In the above steps, the exercise program may include one or more exercise modes and a recommended exercise duration corresponding to each exercise mode. The exercise program may also include an exercise heart rate, an estimated calorie consumption, an exercise grouping situation, and so on. The exercise grouping situation refers to subdivision of an exercise mode. For example, when the exercise category corresponding to an exercise mode is a strength exercise, the exercise grouping situation may include 2~3 groups of supine knee flexion, 8-12 per group; 2~3 groups of air kicking, 8-12 per group; 2~3 groups of bench press, 8-12 per group. Subdividing an exercise mode by means of an exercise grouping situation may provide the user with more accurate exercise recommendation information.

The evaluation attribute list may include a plurality of evaluation attributes corresponding to an exercise mode.

In some embodiments, the exercise risk level of the user may be determined according to the basic information of the user, and at least one exercise program is then ranked according to the plurality of evaluation attributes and the exercise risk level.

In some embodiments, ranking the at least one exercise program according to the plurality of evaluation attributes and the exercise risk level may comprise:

acquiring a weight coefficient corresponding to each evaluation attribute in the plurality of evaluation attributes of each exercise mode;

calculating a weighted sum based on the weight coefficients corresponding to the plurality of evaluation attributes and the values corresponding to the plurality of evaluation attributes to obtain a first multiplication result;

multiplying the value of the exercise risk level corresponding to each exercise mode by the weight coefficient corresponding to the exercise risk level to obtain a second multiplication result;

taking the sum of the first multiplication result and the second multiplication result as an evaluation index of each exercise mode in the at least one exercise program;

determining a comprehensive evaluation index of each exercise program according to the evaluation index of each exercise mode and the weight coefficient corresponding to each exercise mode;

ranking the at least one exercise program according to the comprehensive evaluation index of each exercise program.

In the above steps, the weight coefficient corresponding to the evaluation attribute is to characterize a weight value of the evaluation attribute in the evaluation index calculation.

For example, the evaluation attribute is an exercise intensity value, which accounts for 0.3 in the evaluation index calculation.

The evaluation index K corresponding to each exercise mode is obtained according to the following evaluation index formula:

$K=k_1$*exercise intensity value+$k_2$*whether it is a common exercise+$k_3$*whether equipment is required+$k_4$*exercise difficulty+$k_5$*exercise risk level.

In the above formula, $k_1$ to $k_5$ are the weight coefficients corresponding to the exercise intensity value, whether it is a common exercise, whether exercise equipment is required, exercise difficulty, and the exercise risk level, respectively. $k_1, \ldots, k_5$ may be set based on experience, and the parameter values may also be obtained by training and learning based on historical labeled data.

After obtaining the evaluation index K corresponding to each exercise mode, the comprehensive evaluation index $K_{comprehensive}$ of each exercise program may be determined by the following comprehensive evaluation index calculation formula:

$K_{comprehensive} = a_1 * K_{exercise\ mode1} + a_2 * K_{exercise\ mode2} + \ldots a_N * K_{exercise\ modeN}$ wherein $a_1, a_2, \ldots, a_N$ represents a weight coefficient corresponding to each exercise mode, and its value is in the range of 0~1. $K_{exercise\ mode1}, \ldots, K_{exercise\ modeN}$ represents an evaluation index of each exercise mode, which is may be determined by the above evaluation index calculation formula. N is the number of evaluation methods (i.e. the number of exercise modes).

Finally, the at least one exercise program is ranked according to the comprehensive evaluation index $K_{comprehensive}$ of each exercise program.

In the foregoing embodiment, the exercise programs are ranked by acquiring the comprehensive evaluation index corresponding to each exercise program, which can improve the accuracy of the recommendation result.

In some embodiments, ranking the at least one exercise program according to the plurality of evaluation attributes and the exercise risk level may comprise:

acquiring a weight coefficient corresponding to each evaluation attribute in the plurality of evaluation attributes of each exercise mode;

calculating a weighted sum based on the weight coefficients corresponding to the plurality of evaluation attributes and the values corresponding to the plurality of evaluation attributes to obtain a first multiplication result;

multiplying the value of the exercise risk level corresponding to each exercise mode by the weight coefficient corresponding to the exercise risk level to obtain a second multiplication result;

multiplying the recommended exercise duration of each exercise mode by the weight coefficient corresponding to the recommended exercise duration to obtain a third multiplication result;

taking the sum of the first multiplication result, the second multiplication result, and the third multiplication result as an evaluation index of each exercise mode in the at least one exercise program;

determining a comprehensive evaluation index of each exercise program according to the evaluation index of each exercise mode and the weight coefficient corresponding to each exercise mode;

ranking the at least one exercise program according to the comprehensive evaluation index of each exercise program.

In some embodiments, the recommended exercise duration may also be taken into account in the evaluation index calculation, and the evaluation index K corresponding to each exercise mode may be obtained according to the following evaluation index formula:

$K=k_1$*exercise intensity value+$k_2$*whether it is a common exercise+$k_3$*whether equipment is required+$k_4$*exercise difficulty+$k_5$*exercise risk level+$k_0$*exercise duration/normalization time.

In the above formula, $k_1$ to $k_5$ are the weight coefficients corresponding to the exercise intensity value, whether it is a common exercise, whether exercise equipment is required, the exercise difficulty, and the exercise risk level, respectively. $k_0$ is a weight coefficient of the exercise duration corresponding to the exercise mode, and its value may be determined according to the attributes of the population to which the user belongs. The normalization time refers to a value used to normalize the exercise duration. $k_0, k_1, \ldots, k_5$ may be set based on experience. The parameter values may also be obtained by training and learning based on historical labeled data. The normalization time may be 100, for example.

After the evaluation index K corresponding to each exercise mode is obtained, a comprehensive evaluation index $K_{comprehensive}$ of each exercise program may be determined by the aforementioned comprehensive evaluation index calculation formula. Finally, the exercise programs are ranked according to the comprehensive evaluation index $K_{comprehensive}$.

Step 305: Recommend at least one target exercise program from the ranking result.

In some embodiments provided by the present disclosure, the exercise programs are ranked by acquiring the comprehensive evaluation index of each exercise program, which improves the accuracy of recommending exercises for individual users.

Figure 4:
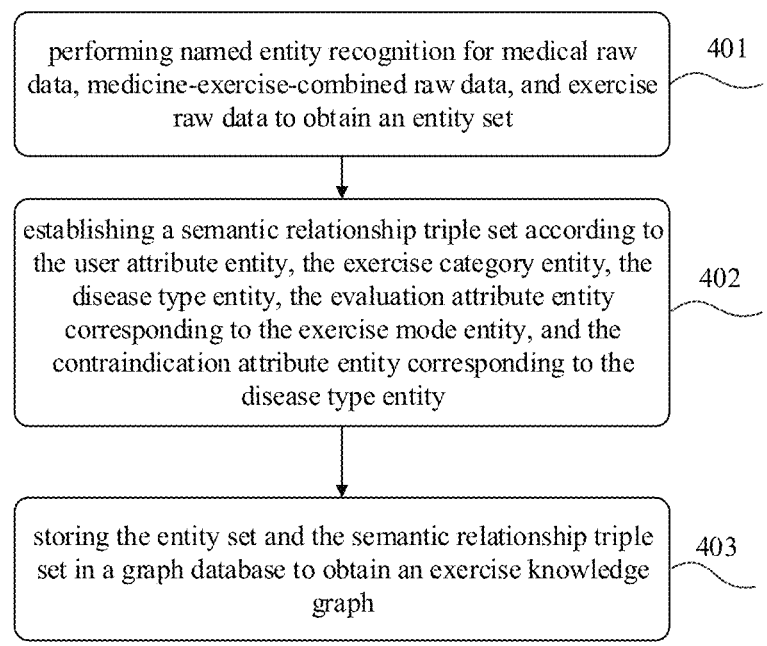
FIG. 4 illustrates a flow chart of establishing an exercise knowledge graph according to an embodiment of the present disclosure.

Some embodiments of the present disclosure further propose a method for establishing an exercise knowledge graph. Referring to FIG. 4, FIG. 4 illustrates a flow chart of a method for establishing an exercise knowledge graph according to an embodiment of the present disclosure. The method comprises the following steps 401-403.

Step 401: Perform named entity recognition for medical raw data, medicine-exercise-combined raw data, and exercise raw data to obtain an entity set. The entity set includes user attribute entities, exercise mode entities, disease type entities, evaluation attribute entities corresponding to exercise mode entities, and contraindication attribute entities corresponding to disease type entities.

Figure 6:
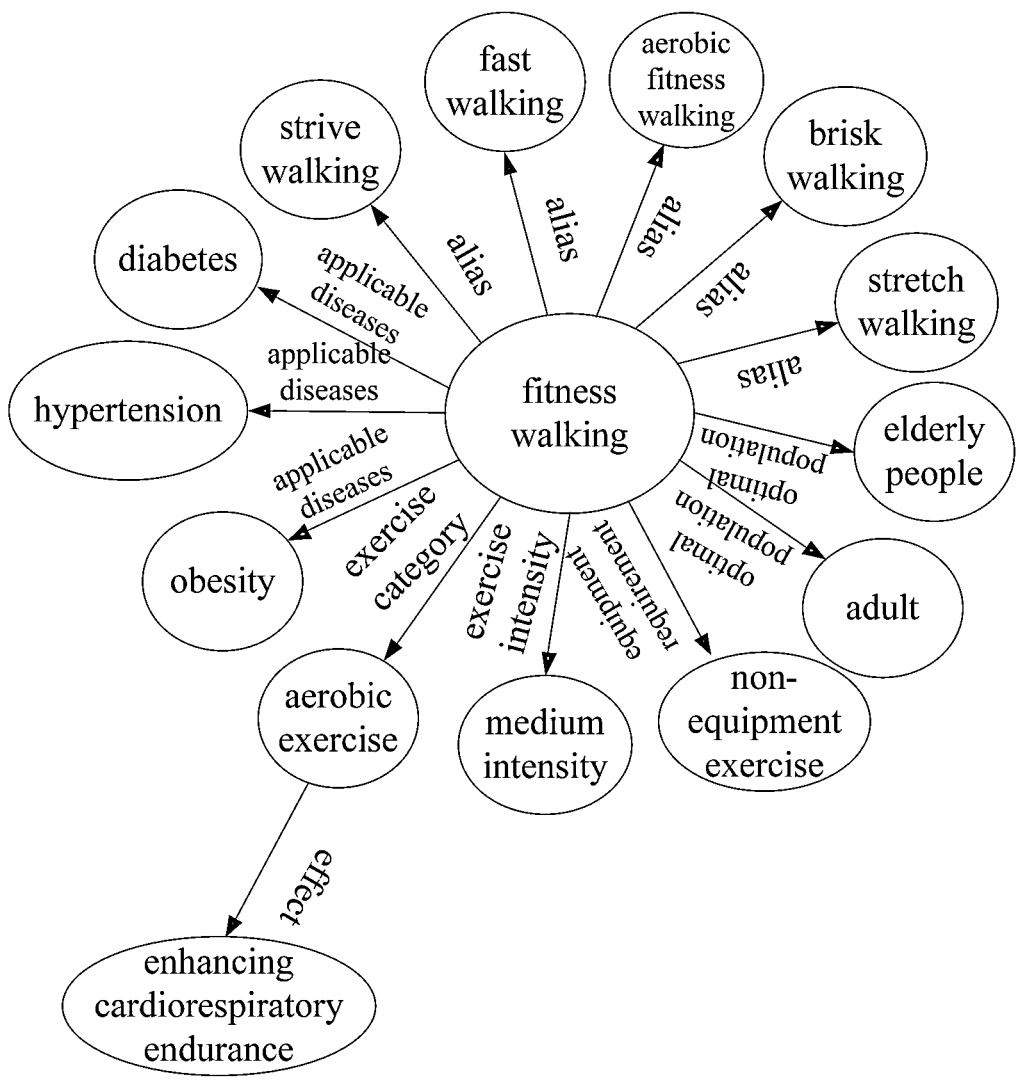
FIG. 6 is a schematic view illustrating a basic relationship between entity names and entity names stored in a graph database according to an embodiment of the present disclosure.
Figure 7:
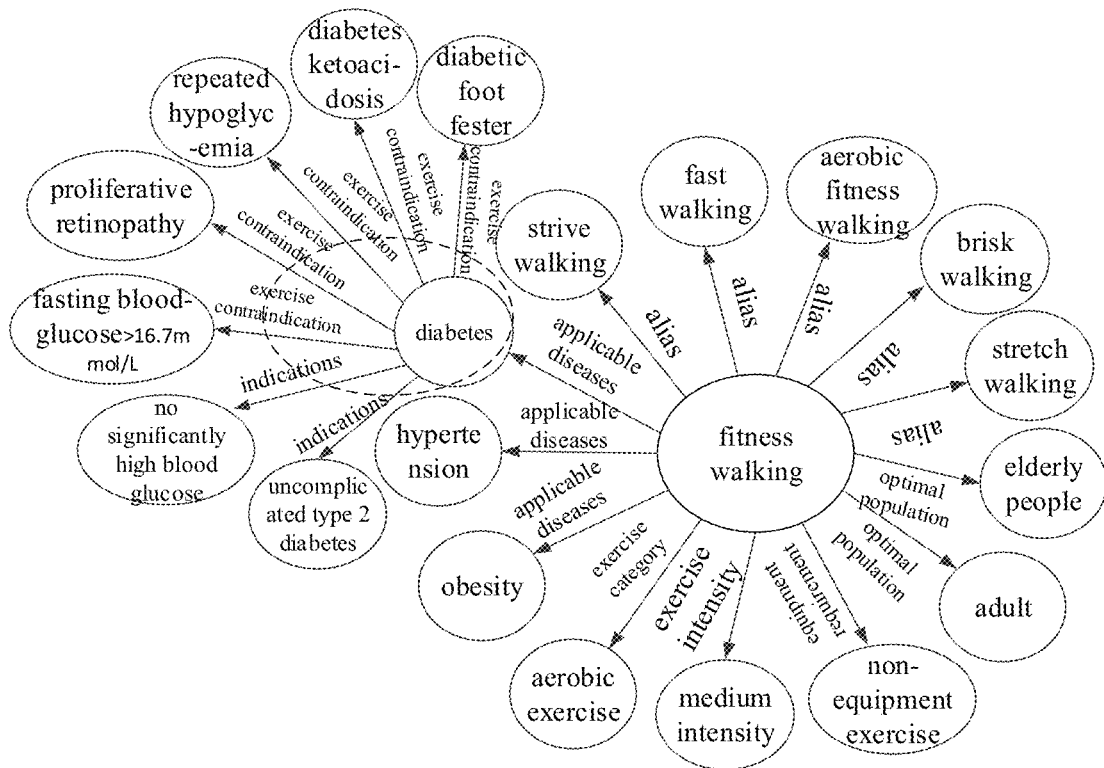
FIG. 7 is a schematic view illustrating another basic relationship between entity names and entity names stored in a graph database according to an embodiment of the present disclosure.
Figure 8:
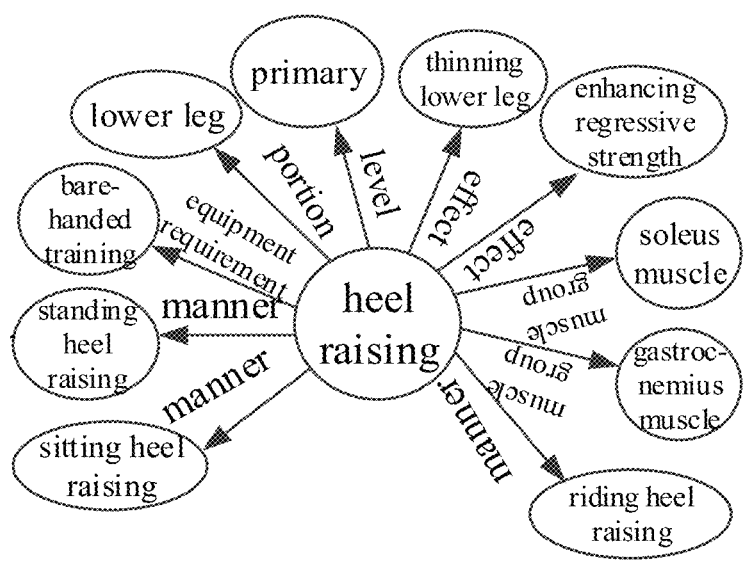
FIG. 8 is a schematic view illustrating a further basic relationship between entity names and entity names stored in the graph database according to an embodiment of the present disclosure.

The user attribute entities include, but are not limited to, adults and elderly people, as shown in FIG. 6. The exercise mode entities include, but are not limited to, fitness walking and heel raising, as shown in FIGS. 6-8. The disease type entities include, but are not limited to, hypertension, diabetes, etc., as shown in FIGS. 6-7. The evaluation attribute entities corresponding to the exercise mode entities include, but are not limited to, an exercise intensity, whether it is an equipment exercise, exercise category, etc., as shown in FIGS. 6-7. The contraindication attribute entities corresponding to the disease type entities include, but are not limited to, exercise contraindications, indications, etc., as shown in FIGS. 6-7.

Figure 9:
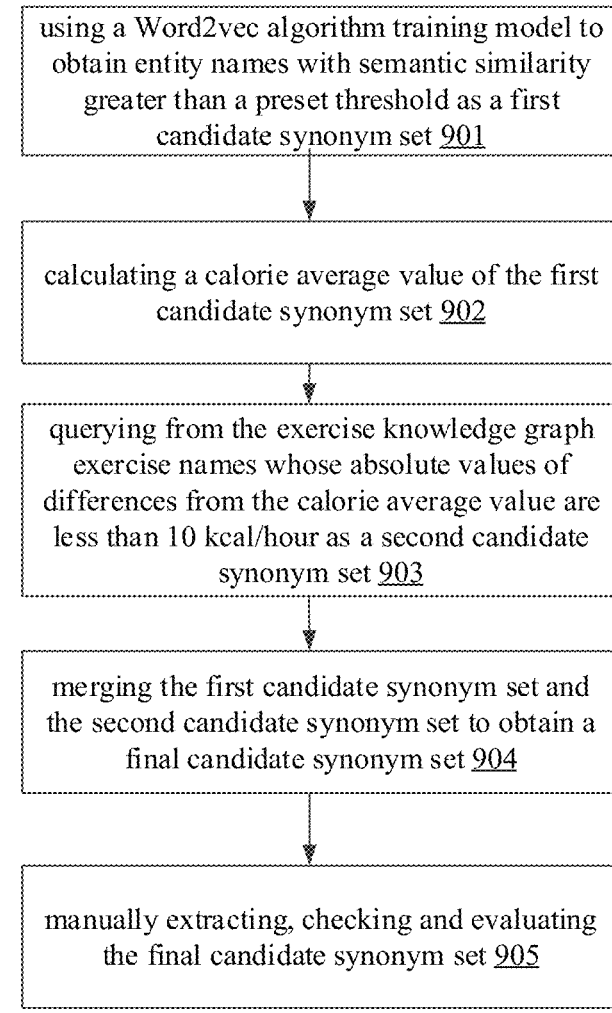
FIG. 9 illustrates a flow chart of a method for processing synonyms of exercise names according to an embodiment of the present disclosure.

During the named entity recognition described above, data to be extracted may be acquired such as clinical medical guidelines, sports medicine books, literature, medical websites, etc. Sports-related named entity recognition (for example, a Bert training model-based BILSTM-CRF algorithm) and relationship extraction (for example, using a Bootstrapping algorithm combined with rule templates) are performed on the data to be extracted. As shown in FIG. 9, in the embodiment of the present disclosure, at step 901, the model may also be trained using a Word2vec algorithm to obtain entity names with semantic similarity greater than a preset threshold as a first candidate synonym set; at step 902, a calorie average value of the first candidate synonym set is calculated; at step 903, exercise names whose absolute values of differences from the calorie average value are less than kcal/hour are queried from the exercise knowledge graph as a second candidate synonym set; at step 904, the first candidate synonym set and the second candidate synonym set are merged to obtain a final candidate synonym set; at step 905, the final candidate synonym set is manually extracted, checked and evaluated. Through the above processing of the synonym sets, multiple synonymous expressions of exercise names corresponding to exercise modes can be obtained, and the ambiguity between multiple synonyms can be eliminated.

Data sources include but are not limited to clinical medicine guidelines, sports medicine books, literature, medical websites, national fitness guidelines, etc. A multi-threaded crawler method may also be used for data crawling and analysis, and data cleaning, merging and integration can be performed.

Step 402: Establish a semantic relationship triple set according to the user attribute entity, the exercise category entity, the disease type entity, the evaluation attribute entity corresponding to the exercise mode entity, and the contraindication attribute entity corresponding to the disease type entity.

The semantic relationship triple set includes a first relationship between the user attribute entity and the exercise category entity, a second relationship between the exercise category entity and the disease type entity, a third relationship between the disease type entity and the contraindication attribute entity corresponding to the disease type entity, and a fourth relationship between the exercise mode entity and the evaluation attribute entity corresponding to the exercise mode entity.

The exercise knowledge graph established in the present disclosure may contain 2684 entities and 10578 triples. The entities may include exercise forms, exercise categories (upper limb, core, stretching, lower limb, strength, yoga, Pilates, etc.), exercise levels, muscle groups, equipment requirements, calories, contraindicated exercises, recommended exercises, suitable populations, action essentials, fitness effects, etc. Entity recognition may employ a Bert pre-training model-based BILSTM-CRF algorithm, which is merged with dictionary data related to diseases, symptoms, exercise modes, actions, human bones, muscles, tissues, diseases, exercise parts, etc. during the process of entity recognition. Relationship extraction may be performed using a Bootstrapping algorithm combined with rule templates.

In some embodiments, for the entities, the relationships between entities and the attribute types included in the exercise knowledge graph, references can be made to Table 1, Table 2 and Table 3, respectively. Table 1 shows the entity types of the exercise knowledge graph. Table 2 shows the relationship between entities of the exercise knowledge graph. Table 3 shows the attribute types of the exercise knowledge graph.

TABLE 1

Entity types of the exercise knowledge graph

| Entity types | meanings | Examples |
| --- | --- | --- |
| symptoms | diseases or symptoms | diabetes |
| action | exercises | running, swimming, Tai Chi, push-ups, etc. |
| is_a | subcategories | practical swimming, competitive swimming, synchronized swimming |
| level | grades | primary, intermediate, advanced |
| category | exercise categories | aerobics, strength, flexibility, etc. |
| equipment | fitness equipment | dumbbells |
| population | populations | female, male, middle-aged, elderly, etc. |
| intensity | intensities | low, medium, high, medium low, medium high |
| effect | functions | fat loss, muscle increase, shaping, blood glucose lowering, etc. |
| alias | exercise aliases | jogging, slow running, running-slow speed |

As shown in Table 1 above, the exercise knowledge graph includes multiple entities, such as diseases, exercise sub-categories, exercise levels, exercise categories, suitable populations, exercise intensities, exercise effects, etc. By extracting multiple exercise-related attributes in an entity manner, the present disclosure provides abundant queryable fields for the query interface, and effectively improves the query efficiency of the exercise knowledge graph.

TABLE 2

Entity relationship types of the exercise knowledge graph

| Entity relationship types | meanings | Examples |
| --- | --- | --- |
| belongs_to | exercises including sub-categories | <jogging, belonging to, running> |
| s2type | exercise categories | <push-ups, category, strength exercises> |
| s2equipment | equipment requirements | <sit-ups, equipment requirement, bare-handed training> |
| s2muscle | main muscle groups | <sit-ups, main muscle group, rectus abdominis> |
| s2othermuscle | related muscle groups | <sit-ups, related muscle group, deltoid> |
| s2level | levels | <sit-ups, level, primary> |
| s2effect | exercise effects | <jogging, exercise effect, fat loss> |
| s2intensity | exercise intensities | <jogging, exercise, intensity, medium intensity> |
| s2Taboo | exercise contraindicated diseases | <running, contraindication disease, hypertension> |
| s2AdapSymptoms | exercise applicable symptoms | <jogging, applicable disease, obesity> |
| s2population | exercise applicable populations | <medical gymnastics, applicable population, elderly> |
| s2alias | exercise aliases | <jogging, alias, running-slow speed> |

As shown in Table 2 above, the exercise knowledge graph includes a variety of entity relationship types, for example, exercises including sub-categories, exercise categories, equipment requirements, main muscle groups . . . exercise effects . . . etc. Through these entity relationships, a plurality of entities are connected to form a graph, and results related to the target search object can be found quickly and accurately using a graph matching query method.

TABLE 3

Attribute types of the exercise knowledge graph

| Attribute types | meanings | Examples |
| --- | --- | --- |
| name | exercise names | jogging |
| desc | exercise introduction | Jogging or Footing, also called... |
| calorie | calorie consumption | 450 kcal/hour |
| point | action essentials | 1. The body is facing forward and upright (not leaning forward or backward). 2. Land on your toes naturally, relax every movement... |
| attention | notes | The exercise intensity should be gradual... |

As shown in Table 3 above, the exercise knowledge graph also provides attribute types, and different attribute types are used to explain the related attributes of an exercise mode. For example, the exercise name, the calorie consumption, the action essentials, etc. can all provide a summary description of an exercise mode, so that the user can understand contents related to the exercise mode. The notes may also be pre-created in the exercise knowledge graph as an attribute of the exercise mode.

At the time of establishing the exercise knowledge graph, as shown in FIG. 6, the synonymous expressions of "fitness walking" include "aerobic fitness walking", "strive walking", "brisk walking", "stretch walking", and so on.

Some contraindication information may also be included in the exercise knowledge graph. The way of extracting the contraindication information includes but is not limited to performing named entity recognition using a Bert pre-training model-based BILSTM-CRF algorithm. The association relationships between the contraindication information, and exercise modes and diseases may be extracted using a Bootstrapping algorithm combined with rule templates.

For example, for the text "Epilepsy needs to avoid dangerous exercises such as skiing, diving and the like. It is forbidden to swim on the beach or in the river. It is not suitable to work at height and operate machinery.", the disease of "epilepsy" and the exercise modes of "skiing", "diving" and "swimming" can be identified through named entity recognition, and semantic relationship triples of "epilepsy-contraindicated exercise-skiing", "epilepsy-contraindicated exercise-diving", and "epilepsy-contraindicated exercise-swimming" can be extracted through relationship extraction.

For the text "Low back pain is classified into acute low back pain and chronic low back pain. If it is acute low back pain, too strenuous exercises cannot be taken, and daily life is suggested. If it is chronic low back pain, exercises can be taken to relieve low back pain. Swimming is recommended because swimming has the least load on the lumbar spine. It is not suggested to play basketball, badminton, etc. because they may cause an injury, especially for people with a larger body weight. If there is no condition for swimming, plank exercise may be done at home to strengthen lumbar and abdominal muscles, i.e. the core muscles. Tai Chi is capable of training the core muscles and also good for balance.", "low back pain", "acute low back pain" and "chronic low back pain" are obtained through named entity recognition, and "chronic low back pain-recommended exercise-swimming", "chronic low back pain-recommended exercise-plank", "chronic low back pain-recommended exercise-Tai Chi", "chronic low back pain-contraindicated exercise-basketball", "chronic low back pain-contraindicated exercise-badminton" can be extracted through relationship extraction.

Step 403: Store the entity set and the semantic relationship triple set in a graph database to obtain an exercise knowledge graph.

The above entity set includes, but is not limited to, user attribute entities, exercise mode entities, disease type entities, evaluation attribute entities corresponding to exercise mode entities, and contraindication attribute entities corresponding to disease type entities.

The above semantic relationship includes, but is not limited to, a first relationship between the user attribute entity and the exercise category entity, a second relationship between the exercise category entity and the disease type entity, a third relationship between the disease type entity and the contraindication attribute entity corresponding to the disease type entity, and a fourth relationship between the exercise mode entity and the evaluation attribute entity corresponding to the exercise mode entity.

The above named entity recognition results and relationship extraction results are stored in a graph database to obtain an exercise knowledge graph. For example, a Neo4j graph database is used for storage.

As shown in FIGS. 6-7, taking fitness walking as an example of the exercise mode, a plurality of semantic relationship triples can be established according to various attributes such as the alias, applicable populations, exercise category, applicable diseases, etc. corresponding to fitness walking. Each semantic relationship triple may represent a relationship attribute between two entities. For example, the first relationship between the user attribute entity and the exercise category entity may be expressed as <fitness walking, optimal population, elderly>. The second relationship between the exercise category entity and the disease type entity may be expressed as <fitness walking, applicable disease, diabetes>. The third relationship between the disease type entity and the contraindication attribute entity corresponding to the disease type entity may be expressed as <diabetes, exercise contraindications, repeated hypoglycemia>. The fourth relationship between the exercise mode entity and the evaluation attribute entity corresponding to the exercise mode entity may be expressed as <fitness walking, exercise intensity, medium intensity>, <fitness walking, default, per unit calorie consumption>, and so on.

The exercise modes and the attribute relationships are stored in a graph database as a named entity recognition result and a relationship type extraction result respectively, thereby establishing an exercise knowledge graph proposed by the embodiment of the present disclosure.

The exercise knowledge graph proposed by the embodiment of the present disclosure can realize screening of exercise modes associated with a target disease type according to the contraindication attribute of the target disease type, and convert the exercise clinical guidance into an achievable recommendation strategy through the contraindication attribute, which effectively improves the accuracy of exercise mode recommendation.

In order to understand the exercise recommendation method proposed by the present disclosure more clearly, the exercise recommendation method will be described in detail with reference to FIGS. 5-17 based on an example of a physical examination result and a questionnaire result of a male.

Figure 5:
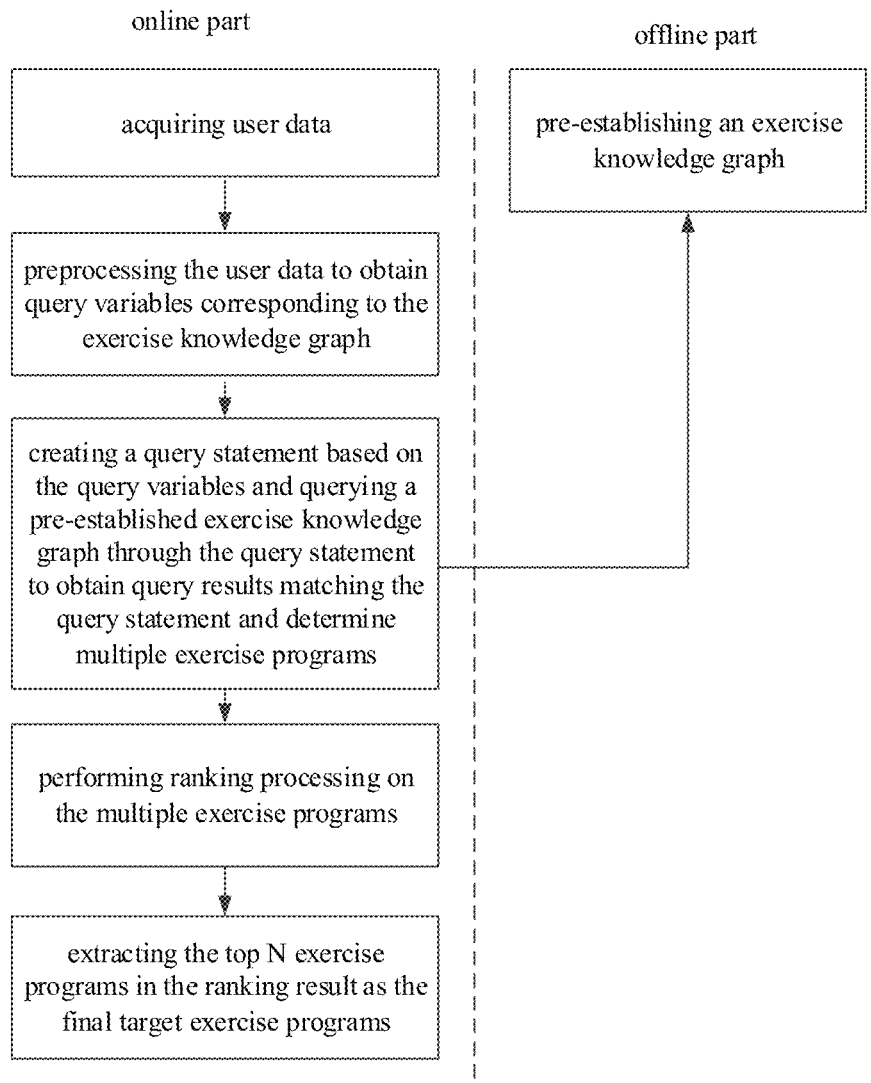
FIG. 5 illustrates a flow chart of a further exercise recommendation method according to an embodiment of the present disclosure.

As shown in FIG. 5, the overall exercise recommendation method may include an offline part and an online part. The offline part can be used to realize the establishment of the exercise knowledge graph, and the online part is an application of the exercise knowledge graph established by the offline part.

The following mainly describes the online part.

As shown in FIG. 5, user data may be acquired, and the user data includes but is not limited to user physical examination data. Further, it is possible to determine the electronic questionnaire content to be provided according to the user physical examination data, and obtain answers (i.e., questionnaire data) to the electronic questionnaire content, as shown in 1001 of FIG. 10. The physical activity level assessment result of the user is then obtained according to the answers (i.e., questionnaire data) to the electronic questionnaire content, which can be shown as 1002 of FIG. 10.

It is assumed that the user physical examination data is acquired as follows:
Sex: Male
Age: 66
Height: 176 cm
Weight: 70 kg
Exercise contraindications: none.

The electronic questionnaire content provided to the user according to the user's age includes PAR-Q questionnaire content and the PAR-Q questionnaire content may be provided to the user in a voice interaction manner. After the voice response result of the PAR-Q questionnaire content is obtained, the voice response result is analyzed to obtain that the physical activity level assessment result of the user is a medium level.

Figure 10:
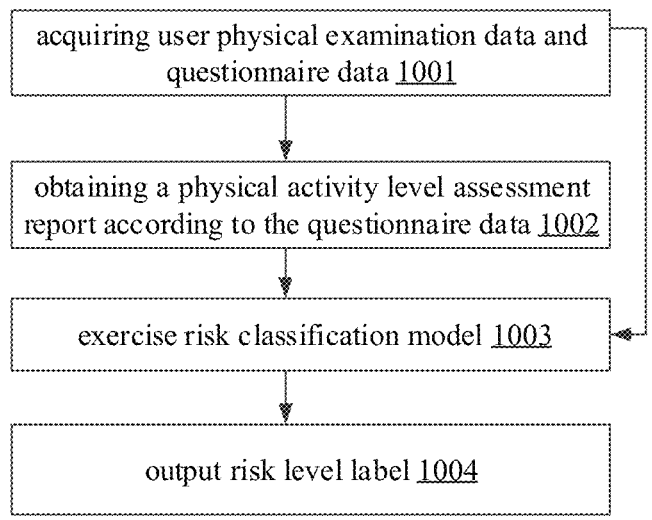
FIG. 10 illustrates a flow chart of an exercise risk classification processing method according to an embodiment of the present disclosure.

As shown in 1003 of FIG. 10, after the physical examination data and the physical activity level assessment result of the user are processed by an exercise risk classification model, the exercise risk assessment result of the user is obtained at 1004 to be medium, that is, the risk level label is a medium risk.

The exercise risk classification model includes, but is not limited to, a deep learning model obtained by training using an AdaBoost algorithm. The exercise risk level of the user can be represented by a risk level label. The risk level label includes but is not limited to four categories: no risk, low risk, medium risk, and high risk.

The AdaBoost algorithm can train multiple weak classifiers and linearly combine the weak classifiers to obtain a strong classifier. The weak classifier here uses a classification and regression tree.

When the exercise risk classification model is being trained, input data includes but is not limited to: basic information: gender, age, occupation; health history: family history, current medical history, allergy history, medication history, surgery history, menstruation and childbirth history (female), body symptoms; physical examination information: height, weight, waist circumference, hip circumference, systolic blood pressure, diastolic blood pressure, heart rate, fasting blood glucose (FPG), postprandial blood glucose (2HPG), glycosylated hemoglobin, total cholesterol, triglycerides, high-density lipoprotein cholesterol, low-density lipoprotein cholesterol, intrahepatic fat content, blood uric acid, bone density; living habits: diet, exercise, sleep, smoking, drinking; environment: humidity, PM2.5, etc., and the physical activity level (IPAQ) is obtained through questionnaire evaluation.

The physical state may be calculated by height, weight and waist circumference. The specific calculation method is as follows:

| Name | Calculation method (persons between 18 and 65 years old) |
| --- | --- |
| thin | BMI < 18.5 |
| normal | 18.5 ≤ BMI < 24 |
| overweight | 24 ≤ BMI < 28 |
| obesity | 28 ≤ BMI |
| central obesity (abdominal obesity) | waist circumference: male ≥ 90 CM, female ≥ 85 CM |
| pre-central obesity | waist circumference 85 cm ≤ male < 90 cm, 80 cm ≤ female < 85 cm |

BMI calculations for other ages refer to international calculation standards. It is possible to know about the blood glucose status of the user through the relationships between fasting blood glucose, glycosylated hemoglobin and diabetes, thereby determining whether there is an important indicator of abnormal blood glucose.

The above systolic blood pressure and diastolic blood pressure are important indicators for determining whether the user has high blood pressure or increased blood pressure. For another example, blood uric acid is an important indicator for determining whether the user suffers from gout; bone density is an important indicator for determining whether the user has osteoporosis, and this indicator can also determine the severity of osteoporosis. The intrahepatic fat content is an important indicator for determining whether the user has fatty liver or abnormal blood lipid. If there is no bone density, OSTA (osteoporosis self-screening tool for Asians) may be used to predict the risk of osteoporosis based on age and weight.

The above exercise risk classification model may also incorporate some expert knowledge during the training phase. For example, the clinical guidelines point out: for 18<=age<=40, if there is no medical history, medication, etc., there is no need to perform exercise ability assessment, there is no need to push the PAR-Q questionnaire content to the user, and there is no need to refer to the PAR-Q questionnaire result when performing exercise ability assessment. For age>40, it is necessary to perform exercise ability assessment, the PAR-Q questionnaire content may be pushed to the user, and the PAR-Q questionnaire result is combined when performing exercise ability assessment. In some embodiments, for individuals of any age, if they do not usually exercise or suffer from a certain disease or have a potential disease, it is necessary to perform exercise risk assessment before starting exercise and increasing the amount of activity.

However, the user data is only preprocessed to obtain query variables corresponding to the exercise knowledge graph. For example, according to the age value in the user physical examination data, it can be determined that the user belongs to elderly people. That is, according to the age of 66, the user is determined to be an elderly person, which is expressed as a query variable of "elderly". According to the height, weight and waist circumference of the user, it can be determined that the physique level of the user is obesity. Optionally, it may also be determined whether there is central obesity according to the waist circumference. That is, according to height: 176 cm and weight: 70 kg, the BMI of the user is determined to be obesity, which is expressed as a query variable of "obesity". It is determined whether there is significantly high blood glucose according to fasting blood glucose. It is determined whether there is significant hypertension according to diastolic blood pressure and systolic blood pressure. If one of "whether there is significantly high blood glucose" and "whether there is significant hypertension" is positive, it is determined that the user does not need to exercise for the time being, and it is suggested to take exercises again after the blood glucose and blood pressure have stabilized. As an example, by preprocessing the above user physical examination data, the query variables can be obtained as follows:

Sex: Male;
Belonging to the population: elderly;
BMI status: obesity;
Disease condition: diabetes;
Physical activity level: medium;
Exercise contraindications: none;
Exercise risk assessment result: medium;
Whether there is significantly high blood glucose: no;
Whether there is significant hypertension: no.

Next, after obtaining the above query variables, a query statement is created based on the query variables, and the pre-established exercise knowledge graph is queried through the query statement to obtain query results that match the query statement, that is, to obtain a target exercise mode list including exercise modes, an evaluation attribute list including evaluation attributes corresponding to the target exercise mode list. Then, multiple exercise programs are determined on this basis.

As an example, from the knowledge graph (only part of which is shown) as shown in FIG. 7, an exercise mode list that satisfies the diseases or symptoms being "obesity" and "diabetes", and the applicable population being "elderly" is queried. Taking the target user attribute and the target disease type as query conditions, a first query statement is created as follows:

```
MATCH (a:Action)-[r:s2AdapSymptoms]->(s:Symptoms) where
s.name="obesity" and s.name="diabetes" WITH a,r,s MATCH
(a:Action)-[r1:s2population]->(p:population) where p.name="elderly"
return a,r,s,r1,p LIMIT 10
```

The query return result a (to distinguish, set action_list=a) is:

```
action_list= ["brisk walking", "medical gymnastics", "Tai Chi", "Ba
Duan Jin", "running", "swimming", "square dance", "playing basketball",
"playing Badminton", "aerobics"].
```

An exercise mode list that can be recommended to the user is obtained through the above query statement, wherein "brisk walking", "medical gymnastics", "Tai Chi" and so on are exercise modes.

The action_list is filtered by "physical activity level assessment result: medium" to obtain an exercise mode that satisfies the exercise intensity being "low intensity" or "medium intensity". Taking the physical activity level assessment result of the user as a query condition, a second query statement is created as follows:

```
MATCH (a:Action)-[r:s2intensity]->(s:Intensity) where s.name="low
intensity" or s.name="medium intensity" where a.name in action_list
return a.name, a. calorie, r, s
``` wherein a.name is the exercise name, and a.calorie is the calorie consumption per hour (in kcal).

After the above filtering process, the filtered exercise mode list and the per unit calorie consumption list corresponding to the exercise mode list are:

```
a.name list = ["brisk walking", "Tai Chi", "medical gymnastics", "Ba
Duan Jin", "running", "square dance", "playing badminton", "aerobics"]
a.calorie list=["228 kcal/hour", "180 kcal/hour", "240 kcal/hour", "270
kcal/hour", "670 kcal/hour", "180 kcal/hour", "270 kcal/hour", "354
kcal/hour"].
```

In some embodiments, it is only required to take the target user attribute and the target disease type as query conditions, and the first query statement is created as follows:

```
MATCH (a:Action)-[r:s2AdapSymptoms]->(s:Symptoms) where
s.name="obesity" and s.name="diabetes" WITH a,r,s MATCH
(a:Action)-[r1:s2population]->(p:population) where p.name="elderly"
return a.name,a.calorier,s,r1,p LIMIT 10
``` wherein a.name is the exercise name, and a.calorie is the calorie consumption per hour (in kcal).

The target calorie consumption of 340 kcal input by the user at the human-computer interaction interface is acquired, and the exercise program of the user is determined according to the target exercise mode list, the evaluation attribute list, and the target calorie consumption. For the user's "physical activity level assessment level: medium", two exercise modes are obtained from the filtered exercise mode list. Then, a combination result of the recommended exercise durations corresponding to the exercise modes is determined according to the recommended exercise duration formula.

It is assumed that "brisk walking" and "Tai Chi" are obtained from the a.name list (i.e. the exercise mode list) as an exercise combination result, where $c_{brisk\ walking}$ represents a per unit calorie consumption corresponding to "brisk walking", and $c_{Tai\ Chi}$ represents a per unit calorie consumption corresponding to Tai Chi.

According to the formula $y=c_{brisk\ walking}*t_{brisk\ walking}+c_{Tai\ Chi}*t_{Tai\ Chi}$, the exercise combination result of the user is determined as follows:

$t_{brisk\ walking}=30$; $t_{Tai\ Chi}=50$
$t_{brisk\ walking}=40$; $t_{Tai\ Chi}=45$ wherein the value of the exercise duration is taken from [10, 15, 20, . . . , 85, 90], and the exercise duration corresponding to the exercise mode may be determined within this time range. For example, the time step corresponding to "brisk walking" is preferably 10 minutes. When the recommended exercise duration corresponding to "brisk walking" is 30 minutes, according to the above formula, taking the target calorie consumption of 340 kcal as a restrictive condition, it can be determined that the recommended exercise duration corresponding to "Tai Chi" is 50 minutes. The recommended exercise duration corresponding to "brisk walking" is then increased by 10 minutes to obtain that the recommended exercise duration corresponding to "brisk walking" is 40 minutes. Thus, according to the above formula, taking the target calorie consumption of 340 kcal as a restrictive condition, it can be determined that the recommended exercise duration corresponding to "Tai Chi" is 45 minutes. By taking the target calorie consumption of 340 kcal as a restrictive condition, multiple recommended time combinations corresponding to an exercise combination result are determined, and multiple exercise programs are obtained.

According to the target exercise mode list, the evaluation attribute list, and the target calorie consumption, multiple exercise programs Z are determined as follows:

Z={[("brisk walking", 30),("Tai Chi", 50)],[("brisk walking", 40),("Tai Chi", 45)], ...... }.

The above multiple exercise programs are then ranked.

It is assumed that the evaluation attribute set corresponding to "brisk walking" includes {exercise intensity value: 3.8; whether it is a common exercise: 1; whether exercise equipment is required: 0; exercise difficulty: 0; user exercise risk level: 0}. For whether it is a common exercise: if it is, the value is 0; if not, the value is 1. For whether exercise equipment is required: if it is, the value is 0; if not, the value is 1. For exercise difficulty: if it is low, the value is 0; if it is medium, the value is 1; if it is high, the value is 2. For user exercise risk level: if there is no risk, the value is 0; if it is a low risk, the value is 1; if it is a medium risk, the value is 2; if it is a high risk, the value is 3.

The exercise intensity value of "brisk walking" can be determined by querying the exercise knowledge graph. For example, the following query statement is used to query the exercise knowledge graph, MATCH (a:Action{name:"brisk walking"}) RETURN a.mets;

to obtain the exercise intensity of "brisk walking" mets=3.8.

Then, according to the following evaluation index formula, the evaluation index $K_{brisk\ walking}$ corresponding to "brisk walking" is determined as:

$$K_{brisk\ walking}=0.3*3.8+0.2*0+0.1*1+0.2*0+0.2*0+0.3*30/100=1.33.$$

The evaluation index corresponding to each exercise mode in the exercise combination result can be calculated through the above similar process, such as "Tai Chi" in the exercise combination result ("brisk walking", "Tai Chi").

Then, according to the following comprehensive evaluation index formula, a comprehensive evaluation index $K_{comprehensive}$ corresponding to the exercise combination result ("brisk walking", "Tai Chi") is determined, $$K_{comprehensive}=a_1*K_{brisk\ walking}+a_2*K_{Tai\ Chi}$$

In the above formula, $a_1$ represents a weight coefficient corresponding to brisk walking, and its value is, for example, 0.3; $a_2$ represents a weight coefficient corresponding to Tai Chi, and its value is, for example, 0.7.

As an example, an exercise program set {[("brisk walking", 30), ("Tai Chi", 50)], [("brisk walking", 40), ("Tai Chi", 45)], . . . } is ranked in a descending order according to the comprehensive evaluation index (that is, the comprehensive evaluation indexes are ranked from high to low), wherein [("brisk walking", 30), ("Tai Chi", 50)] is an exercise program, and the exercise program set includes multiple exercise programs. Firstly, according to the above comprehensive evaluation index formula, a comprehensive evaluation index is calculated for each exercise program, and the exercise programs are ranked according to the comprehensive evaluation indexes from high to low to obtain a ranking result {[[("brisk walking", 40),("Tai Chi", 45)],("brisk walking", 30), ("Tai Chi" 50)], . . . }.

Finally, the top N exercise programs are taken from the ranking result as a final target exercise program. The value of N is related to the physical activity level assessment result of the user, and the value of N may be a natural number such as 1, 2, 3, etc. For example, in the above embodiment, if the user is an elderly person, the two highest-ranked exercise programs may be taken from the ranking result as the target exercise programs.

Through the above processings, the exercise combination results are preferably selected and ranked according to the basic information of the user, and a personalized recommendation result more suitable for the user is obtained. Compared with the way of recommending exercises to the user in the related art, the embodiments of the present disclosure can accurately provide the user with highly applicable exercise combination results, thereby improving the accuracy of the exercise recommendation result.

In some embodiments, as shown in FIG. 16, an exercise plan may also be recommended to the user. The exercise plan refers to a set of exercise programs recommended to the user during the exercise planning period according to the exercise frequency recommended by the guidelines. The exercise planning period refers to the length of time of a periodic exercise performed by the user. For example, the length of the exercise planning period is one week, i.e., a weekly exercise plan. Taking a user as an example below, the user physical examination data is age: 66, gender: male, height: 176 cm, weight: 70 kg, and waist circumference: 88 cm. It is assumed that a weekly exercise plan is recommended to the user, and the exercise planning period is 7 days.

The exercise planning period and the exercise frequency are acquired. The exercise planning period may be input by the user or set by the system by default. The exercise frequency refers to the number of times of exercise within the exercise planning period. The exercise frequency may be an optimal number of times of exercise within the exercise planning period determined according to the user physical examination data and the questionnaire data. For example, if the exercise planning period is 7 days, the user age in the user physical examination data is 66 years old, and the physical activity level assessment result obtained from the questionnaire data is a medium level, it can be determined (for example, it can be determined according to a pre-established relationship table of the user age, the physical activity level assessment result and the exercise frequency) that the exercise frequency corresponding to an elderly person and the physical activity level assessment result being a medium level is 4, that is, the exercise frequency is 4 times within 7 days of the exercise planning period.

In some embodiments, the exercise frequency may also be determined according to a pre-established relationship table of the user age, the physical activity level assessment result, the exercise category, and the exercise frequency. For example, if the user is a young person, the physical activity level assessment result is a medium level, and the exercise category is aerobic exercise and strength exercise, it is determined that the exercise frequency of aerobic exercise of the user within 7 days of the exercise planning period is 6 times, and the exercise frequency of strength exercise is 4 times.

When a recommended exercise duration corresponding to an exercise mode is allocated according to the exercise planning period, the exercise planning period and the exercise frequency are acquired, the maximum activity amount and the minimum activity amount corresponding to the exercise planning period are determined, and a time array is determined according to the maximum activity amount and the minimum activity amount.

The time array includes the exercise frequency and a recommended exercise duration corresponding to the exercise frequency, and the expression mode of the time array includes but is not limited to [exercise duration, exercise frequency], [recommended exercise duration], etc. A qualified time array is obtained according to the following time array determination formula:

$$v_1 \le \sum_{i=1}^{f} t_i \le v_2.$$

As in the above formula, it is assumed that the time array is T=[ti,f], the exercise frequency is f times, the minimum activity amount corresponding to the exercise planning period is $v_1$, the maximum activity amount corresponding to the exercise planning period is $v_2$, and $t_i$ represents a suggested length of time of exercise taken by the user each time. The time units of $t_i$, $v_1$ and $v_2$ are minute, and the unit of f is the number of days or times.

The maximum activity amount and the minimum activity amount corresponding to the exercise planning period may be obtained by querying the pre-established exercise knowledge graph according to the user physical examination data, the questionnaire data and the exercise risk assessment result.

It is assumed that a preset time selection range is $T_{range}$= [10, 15, 20, . . . , 90]. $t_i$ can repeatedly acquire a recommended exercise duration from the time selection range to obtain a time array.

For example, if the time array is [35,4], it means acquiring 35 minutes 4 times from the time selection range, and the recommended exercise durations corresponding to the exercise modes are all 35 minutes. 4 times means that the user needs to take exercise 4 times within the exercise planning period.

For another example, the time array [15,25,35,45] means acquiring 15 minutes, 25 minutes, 35 minutes and 45 minutes from the time selection range as recommended exercise durations corresponding to the respective exercise modes.

In the following description, it is assumed that the user's time array T=[35,4] is obtained according to the above time array determination formula.

In some embodiments, the target dates corresponding to the exercise combination result may be allocated within the exercise planning period according to the time array T. For example, it is possible to first determine a recommended exercise duration corresponding to each exercise mode in the exercise combination result, and then determine the target dates corresponding to the exercise combination result in the exercise planning period according to the exercise frequency.

For example, for a user who is an elderly person aged 66 years old, when the number n of exercise modes included in the exercise combination result is 1, it is determined that the recommended exercise duration corresponding to each exercise mode in the exercise combination result is:
 if the exercise combination result is "brisk walking", it is recommended to take exercise for 35 minutes each time, 4 times a week;
 if the exercise combination result is "Tai Chi", it is recommended to take exercise for 40 minutes each time, 4 times a week.

Then, the target dates corresponding to the exercise combination result in the exercise planning period are determined according to the exercise frequency, that is, the target dates corresponding to "brisk walking" are determined as follows:

Monday: "brisk walking" 35 minutes
Wednesday: "brisk walking" 35 minutes
Thursday: "brisk walking" 35 minutes
Saturday: "brisk walking" 35 minutes.

The target dates corresponding to "Tai Chi" are determined as follows:
Tuesday: "Tai Chi" 40 minutes
Wednesday: "Tai Chi" 40 minutes
Friday: "Tai Chi" 40 minutes
Sunday: "Tai Chi" 40 minutes.

In some embodiments, it is assumed that two exercise modes are obtained from the ranked target exercise mode list as the exercise combination result, that is, the exercise combination result is ("brisk walking", "Tai Chi") and the recommended total exercise duration corresponding to the exercise combination result is 45 minutes. The recommended exercise duration corresponding to each exercise mode is determined according to the number of exercise modes in the exercise combination result. It can be obtained that the recommended exercise durations corresponding to ("brisk walking", "Tai Chi") are [("brisk walking", 25 minutes); ("Tai Chi", 20 minutes))].

For this user, the target dates corresponding to the exercise combination result in the exercise planning period are determined according to the exercise frequency, that is, the target dates corresponding to ("brisk walking", "Tai Chi") are determined as follows:
 Monday: "brisk walking" 25 minutes; "Tai Chi" 20 minutes
 Wednesday: "brisk walking" 25 minutes; "Tai Chi" 20 minutes
 Thursday: "brisk walking" 25 minutes; "Tai Chi" 20 minutes
 Saturday: "brisk walking" 25 minutes; "Tai Chi" 20 minutes.

In some embodiments, the exercise combination result may also be classified according to the exercise category, and then the exercise frequency corresponding to the exercise category is determined. For example, in the case of aerobic exercise f=3, [1, 3, 5] may be selected, that is, taking exercise on Monday, Wednesday and Friday. In the case of strength exercise f=1, a day without aerobic exercise is randomly selected for strength exercise. In the case of strength exercise f=2, strength exercise is allocated to the day with the least aerobic exercise time, and a day without aerobic exercise is randomly selected for another strength exercise. In the case of strength exercise f=3, strength exercise is allocated to 1-2 days with the least aerobic exercise time, and a day without aerobic exercise is randomly selected for remaining strength exercise.

FIG. 15 shows an exemplary presentation interface of an exercise program, and the presentation interface displays an exercise recommendation result suitable for the user. The exercise recommendation result includes the exercise category, the exercise mode corresponding to the exercise category, and the exercise duration corresponding to the exercise category. The corresponding exercise duration, exercise frequency, exercise intensity, etc. may be determined according to the exercise category. The presentation interface includes, but is limited to, a presentation interface in a web page version and an application interface presented by an application pre-installed on the mobile terminal.

For the above male user aged 66 years old, the target exercise planning dates corresponding to the exercise frequency f may be determined in the preset duration according to the exercise category. For example, in the case of aerobic exercise f=4, it can be determined that exercise is taken on Monday, Tuesday, Thursday and Friday.

The embodiments of the present disclosure can effectively improve the accuracy of the exercise recommendation result through the above manner.

In some embodiments, when the user uses the product, the user may also be provided with a query interface such as a visualized interface as shown in FIG. 12 according to the user's requirements. The user can query information related to an exercise mode by directly inputting the exercise name of the exercise mode in the query interface as a keyword. For example, if "Tai Chi" is input, the exercise category, the calorie consumption, the exercise intensity, the metabolic equivalent METs value, the 1000-step activity equivalent, etc. corresponding to "Tai Chi" can be obtained.

In some embodiments, when the user uses the product, the user may also be provided with other query interfaces such as an interactive interface as shown in FIG. 13 according to the user's requirements. The user can select information displayed on the interactive interface or input the weight, exercise duration and exercise mode through the input interface provided within the interactive interface to determine the exercise estimated calorie consumption corresponding to the exercise mode.

For example, the calculation template for the exercise estimated calorie consumption is: weight*exercise duration*metabolic equivalent*0.0167. The metabolic equivalent may be obtained, for example, by querying a pre-established exercise knowledge graph through the acquired exercise mode. For example, if the exercise mode is bicycle riding, the metabolic equivalent METs corresponding to bicycle riding may be obtained by querying the fourth relationship of the exercise knowledge graph, e.g., the exercise mode being bicycle riding (slow speed, 16-19.2 km/h), and the metabolic equivalent being 6.0.

Then, the query parameters acquired by the interface are filled into the calculation template for the exercise estimated calorie consumption to obtain a query result as shown in FIG. 13. In the above calculation template, * represents the multiplication sign, the unit of weight is kilogram, the unit of exercise duration is minute, and the metabolic equivalent, i.e. the value of METs, is a floating point number. If the weight is 60 kilograms, the exercise duration is 40 minutes, and the metabolic equivalent is 6.0, the estimated calorie consumption is 240 kcal.

In some embodiments, the personal information of the user may be input through an interactive interface. The personal information of the user includes but is not limited to the gender, age, height, weight, etc. of the user. As an example, FIG. 14 shows such an interactive interface.

Figure 18:
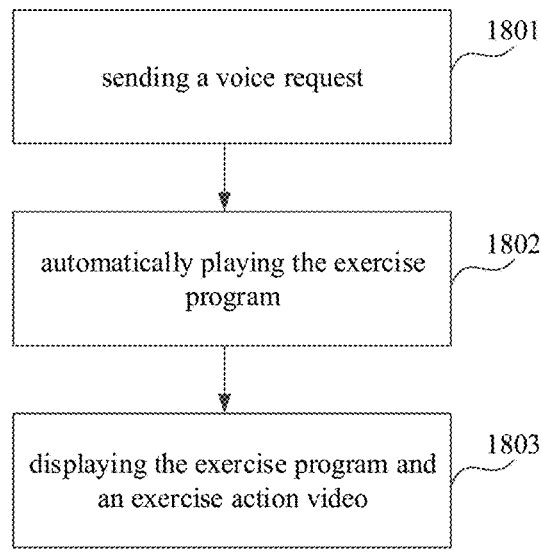
FIG. 18 illustrates a flow chart of a presentation manner of an exercise recommendation result according to an embodiment of the present disclosure.

In order to meet the requirements of different users for using the product, some embodiments of the present disclosure further provide a voice interaction mode. As shown in FIG. 18, when the user sends a "play exercise program" request in step 1801 (for example, a voice request), the system will automatically play the exercise program of the day in step 1802. The exercise program is displayed on the display screen in real time in step 1803. At the same time, the display screen can also display an action video to guide the user to execute the exercise program according to standard actions. The display screen may be a TV, a projector, etc.

In some embodiments of the present disclosure, the exercise heart rate may also be queried through the query interface, wherein the exercise heart rate is calculated by an exercise heart rate calculation template. For example, when the exercise level is low, the exercise heart rate=(220−age)*(50%~60%); when the exercise level is medium, the exercise heart rate=(220−age)*(60%~70%); when the exercise level is high, the exercise heart rate=(220−age)*(70%~80%).

For patients with chronic diseases, sub-health and other diseases, the calculation is carried out in accordance with the exercise frequency range recommended by the exercise prescriptions compiled from the guidelines.

In some embodiments of the present disclosure, the exercise frequency may also be queried through the query interface, wherein, for example, the exercise frequency is determined by an exercise frequency calculation template according to the exercise level. When the exercise level is low, the aerobic exercise frequency f=3 and the strength exercise frequency f=1; when the exercise level is medium, the aerobic exercise frequency f=4 and the strength exercise frequency f=2; when the exercise level is high, the aerobic exercise frequency f=5 and the strength exercise frequency f=2~3. It is required to do stretching training before and after exercise.

As shown in FIG. 8, in some embodiments of the present disclosure, strength exercise querying and recommending methods may also be provided to users. For example, by querying the exercise knowledge graph according to the three fields of exercise portion "lower leg", level "primary", and equipment "bare-handed training", information such as recommended exercise form "heel raising", exercise mode, muscle group, effect, and so on can be obtained.

Figure 17:
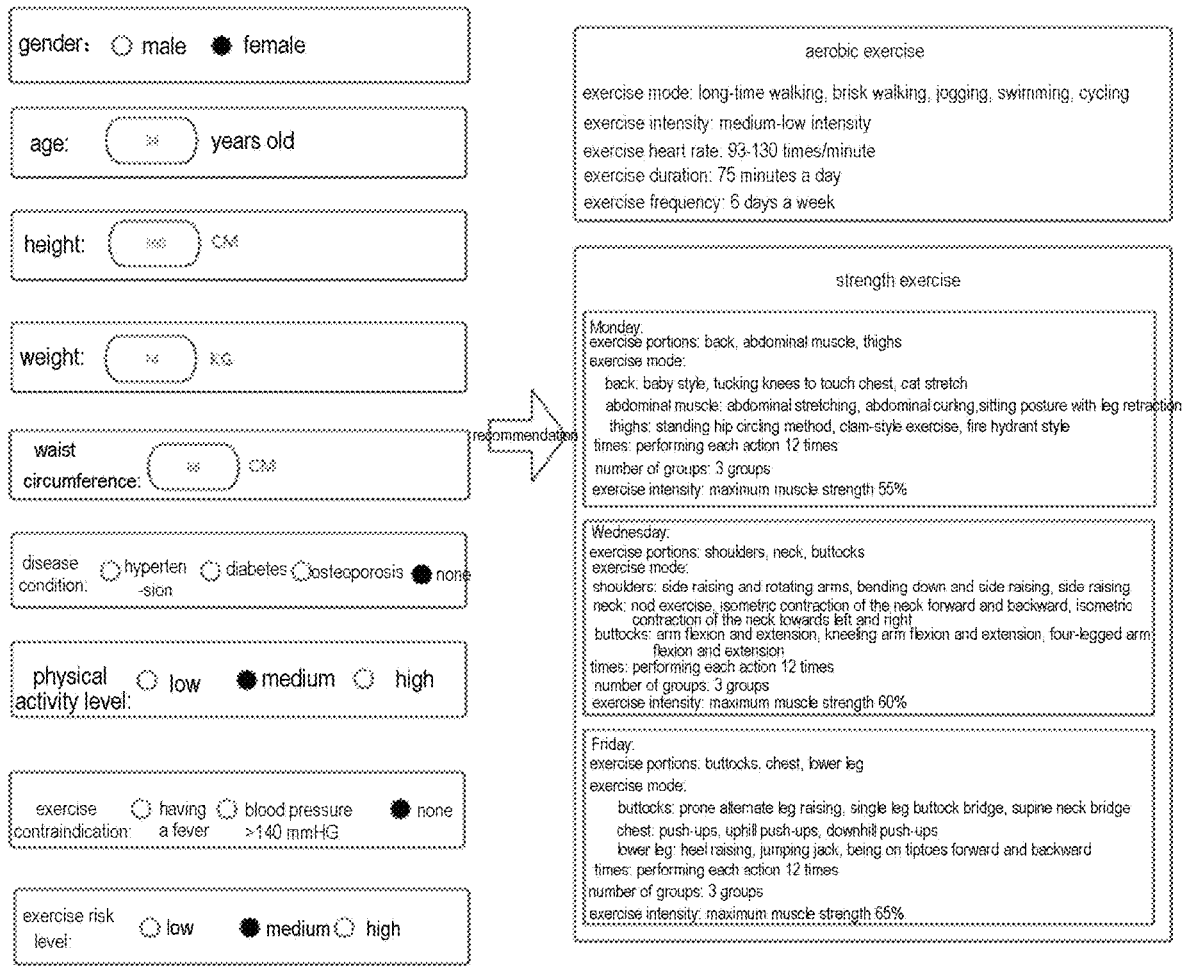
FIG. 17 illustrates a schematic view of an interface presentation for obtaining an exercise recommendation result based on the user physical examination data and questionnaire data query according to an embodiment of the present disclosure.

FIG. 17 shows an exercise plan classified according to exercise categories and obtained according to the physical examination data and physical activity level assessment result of the user provided by some embodiments of the present disclosure. Under each exercise category, exercise modes corresponding to the exercise frequency are allocated according to the exercise frequency. For example, for aerobic exercise, exercise is taken 6 days a week, and the recommended exercise duration is 75 minutes per day. For another example, for strength training, the training position, the number of times of exercise, and the exercise intensity corresponding to the exercise program are presented in detail.

For people suffering from diseases, it is necessary to query knowledge such as exercise contraindications, attentions, etc. in the exercise knowledge graph. For example, for asthma patients, they cannot take exercise in a dry, pollen environment. Therefore, the recommendation model needs to recommend a relatively humid indoor environment for exercise, accurately calculate the exercise heart rate, and emphasize that the patients should not do high-intensity exercise. If it is monitored that the exercise intensity is greater than a certain critical value or autonomous respiration becomes difficult, it reminds the patients to stop doing exercise immediately and provides reasonable treatment suggestions.

In some embodiments, the weather status (humidity, temperature, season, etc.) of the user's location can be obtained, and the user independently selects the exercise environment, like the features such as indoor, outdoor, exercise equipment, bare hands, and so on, to reorder the exercise programs and adjust the exercise programs in real time.

Recommended contents include exercise type, exercise intensity, duration, exercise frequency, exercise heart rate (hr), and total weekly exercise time (v).

In the case where certain field information of the user as variables is unknown or unlimited, for example, in the case that only the gender and age of the user are known, big data is used to analyze exercises suitable for males and females of different ages, which are recommended to the users.

Examples of Recommendation Results:

User 1: age=75, exercise category=aerobic exercise, health status=diabetes, other information is unknown, the recommendation is as follows:

```
{
'type': 'aerobic exercise',
'action': ['slow walking (60-70 steps/minute)'],
'intensity': 'low intensity',
'hr': '87~122 times/minute',
'duration': '30min/time',
'frequency': '2 times/day',
},
{
'type': 'strength exercise',
'action': ['wall push-ups', 'standing elastic belt curling', 'sitting elastic belt flat pushing', 'supine curling', 'standing heel raising', 'half squat', 'standing doing high knees with hands on chair back'],
'intensity': 'medium intensity',
'hr': ['', 'maximum muscle strength 50%~70%'],
'frequency': '2~3 groups a day, 2~3 days a week',
'part': '6~10',
'repeat': '8~12',
};
```

User 2: known data includes: age=13, exercise category=aerobic exercise, health status=obesity, other information is unknown, the recommendation is as follows:

```
{
'type': 'aerobic exercise',
'action': ['long-time walking', 'jogging', 'swimming'],
'intensity': 'medium and low intensity',
}.
```

It is to be noted that although the operations of the method of the present disclosure are described in a specific order in the drawings, this does not require or imply that these operations must be performed in the specific order, or that all the operations illustrated must be performed to achieve the desired result. Conversely, for the steps depicted in the flow chart, the order of execution can be changed. Additionally or alternatively, some steps may be omitted, multiple steps may be combined into one step for execution, and/or one step may be decomposed into multiple steps for execution.

Figure 19:
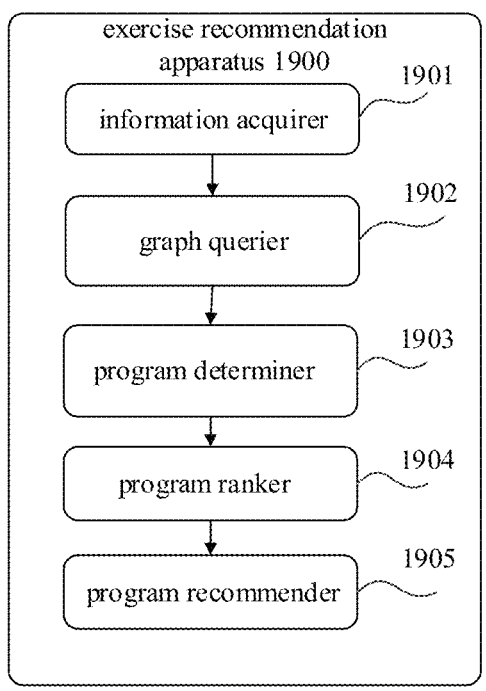
FIG. 19 illustrates a schematic structural view of an exercise recommendation apparatus according to an embodiment of the present disclosure.

Referring to FIG. 19, FIG. 19 shows a schematic structural view of an exercise recommendation apparatus 1900 according to an embodiment of the present disclosure. The device may comprise:

an information acquirer 1901 configured to acquire basic information of a user;

a graph querier 1902 configured to query a pre-established exercise knowledge graph according to the basic information of the user to obtain a target exercise mode list comprising exercise modes, and an evaluation attribute list comprising evaluation attributes corresponding to the target exercise mode list, each evaluation attribute indicating an attribute index for evaluating a corresponding exercise mode;

a program determiner 1903 configured to determine at least one exercise program according to the target exercise mode list and the evaluation attribute list, each exercise program in the at least one exercise program comprising at least one exercise mode and a recommended exercise duration corresponding to the at least one exercise mode;

a program ranker 1904 configured to perform ranking processing on the at least one exercise program according to the evaluation attribute list to obtain a ranking result;

a program recommender 1905 configured to recommend at least one target exercise program according to the ranking result.

It should be understood that each of the information acquirer, the graph querier, the program determiner, the program ranker and the program recommender comprised in the above exercise recommendation apparatus may be a device with processing capabilities such as a processor, a microprocessor, a dedicated integrated circuit, etc. Each device can exist as a unit or module. The units or modules correspond to the steps in the method described with reference to FIG. 2. Therefore, the operations and features described above for the method are also applicable to the above apparatus and the units included therein, which will not be repeated here. The above apparatus may be implemented in a browser of an electronic device or other security applications in advance, and may also be loaded into a browser of an electronic device or other security applications by downloading or the like. The respective units in the above apparatus can cooperate with the units in the electronic device to implement the solutions of the embodiments of the present disclosure.

For the modules or units mentioned in the detailed description above, this division is not mandatory. In fact, according to the embodiments of the present disclosure, the features and functions of two or more modules or units described above may be embodied in one module or unit. On the contrary, the features and functions of a module or unit described above may be further divided into multiple modules or units to be embodied.

Figure 20:
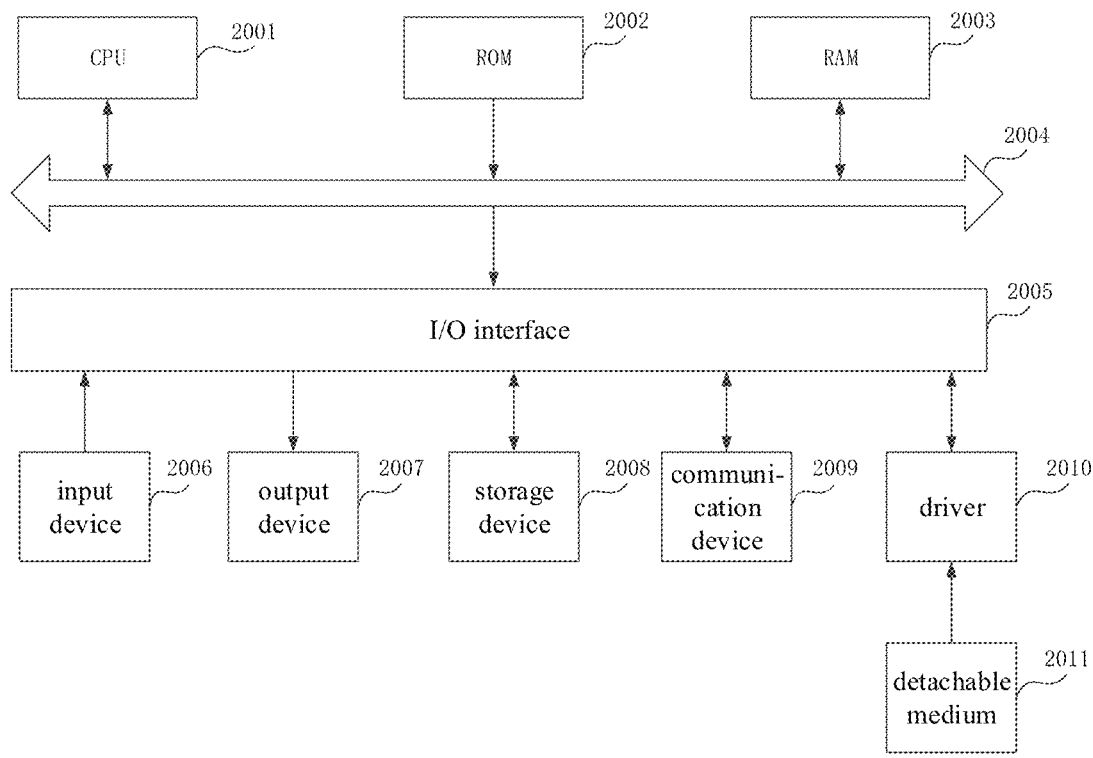
FIG. 20 shows a schematic structural view of a computer system adapted to implement a terminal device or a server according to an embodiment of the present disclosure.

Next, referring to FIG. 20, FIG. 20 shows a schematic structural view of a computer system adapted to implement a terminal device or a server according to an embodiment of the present disclosure.

As shown in FIG. 20, the computer system comprises a central processing unit (CPU) 2001, which can perform various appropriate actions and processings according to computer instructions stored in a read-only memory (ROM) 2002 or computer instructions loaded from a storage device 2008 to a random access memory (RAM) 2003. In the RAM 2003, various computer instructions and data required for the operation of the computer system are also stored. The CPU 2001, the ROM 2002, and the RAM 2003 are connected to each other through a bus 2004. An input/output (I/O) interface 2005 is also connected to the bus 2004.

The following components are connected to an I/O interface 2005: an input device 2006 including a keyboard, a mouse, etc.; an output device 2007 including a cathode ray tube (CRT), a liquid crystal display (LCD), a speaker, etc.; a storage device 2008 including a hard disk, etc.; and a communication device 2009 including a network interface card such as a LAN card, a modem, etc. The communication device 2009 performs communication processing via a network such as the Internet. A driver 2010 is also connected to the I/O interface 2005 as needed. A detachable medium 2011, such as a magnetic disk, an optical disk, a magneto-optical disk, a semiconductor memory, etc., is installed on the driver 2010 as needed, so that the computer instructions read therefrom can be installed into the storage device 2008 as needed.

In particular, according to the embodiment of the present disclosure, the process described above with reference to the flow chart of FIG. 2 may be implemented as a computer software program. For example, an embodiment of the present disclosure comprises a computer program product including computer instructions carried on a machine-readable medium, and the computer instructions include program codes for executing the method shown in the flow chart. In such an embodiment, the computer instructions may be downloaded from the network by the communication device 2009 and installed, and/or installed from the detachable medium 2011. When the computer instructions are executed by the central processing unit (CPU) 2001, the above functions defined in the system of the present disclosure are executed.

It is to be noted that the computer-readable medium shown in the present disclosure may be a computer-readable signal medium or a computer-readable storage medium, or any combination thereof. The computer-readable storage medium may be a transitory storage medium or a non-transitory storage medium. For example, it may be, but not limited to, an electrical, magnetic, optical, electromagnetic, infrared, or semiconductor system, apparatus or device, or any combination thereof. More specific examples of computer-readable storage media may include, but are not limited to: a portable computer magnetic disk, a hard disk, a random access memory (RAM), a read-only memory (ROM), an erasable programmable read-only memory (EPROM or flash memory), an optical fiber, a portable compact disk read-only memory (CD-ROM), an optical storage device, a magnetic storage device, or any suitable combination thereof. In the present disclosure, the computer-readable storage medium may be any tangible medium that contains or stores computer instructions, and the computer instructions may be used by or in combination with an instruction execution system, apparatus or device. In the present disclosure, the computer-readable signal medium may include a data signal propagated in a baseband or as a part of a carrier wave, and computer-readable program codes are carried therein. This propagated data signal may take various forms, including but not limited to an electromagnetic signal, an optical signal, or any suitable combination thereof. The computer-readable signal medium may also be any computer-readable medium other than the computer-readable storage medium. The computer-readable medium may send, propagate or transmit computer instructions for use by or in combination with an instruction execution system, apparatus or device. The program codes contained on the computer-readable medium can be transmitted by any suitable medium, including but not limited to: wireless, wire, optical cable, RF, etc., or any suitable combination thereof.

The flow charts and block diagrams in the accompanying drawings illustrate the architectures, functions and operations of possible implementations of the system, method and computer program product according to various embodiments of the present disclosure. In this regard, each block in the flow chart or block diagram may represent a module, a program segment or a part of a code, and the module, the program segment, or a part of the code contains one or more executable instructions for realizing specified logical functions. It is also to be noted that, in some alternative implementations, the functions marked in the blocks may also occur in a different order from the order marked in the drawings. For example, two consecutive blocks can actually be executed substantially in parallel, or they can sometimes be executed in a reverse order, depending on the functions involved. It is also to be noted that each block in the block diagram and/or flow chart, and a combination of blocks in the block diagram and/or flow chart, can be implemented by a dedicated hardware-based system that performs specified functions or operations, or can be implemented by a combination of dedicated hardware and computer instructions.

The units or modules involved in the embodiments of the present disclosure can be implemented in software or hardware. The described units or modules may also be provided in a processor, for example, it can be described as: a processor comprising an information acquisition unit, a graph query unit, a program determination unit, a program ranking unit, and a program recommendation unit. The names of these units or modules do not constitute a limitation on the units or modules themselves in certain cases. For example, the information acquisition unit may also be described as "a unit for acquiring basic information of a user".

As another aspect, the present disclosure further provides a computer-readable storage medium. The computer-readable storage medium may be included in the electronic device described in the foregoing embodiments, and may also exist independently without being assembled into the electronic equipment. The aforementioned computer-readable storage medium stores one or more computer instructions, which is used to execute the exercise recommendation method described in the present disclosure when the computer instructions are executed by one or more processors.

What have been described are only a part of the embodiments of the present disclosure and explanations of the applied technical principles. Those skilled in the art should understand that the inventive scope involved in the present disclosure is not limited to technical solutions formed by specific combinations of the above technical features, and should also encompass other technical solutions formed by any combinations of the above technical features or their equivalent features without departing from the inventive concept, for example, technical solutions formed by replacing the above features and technical features having similar functions as those disclosed in the present disclosure (but not limited to) with each other.

The invention claimed is:

1. A computer-implemented exercise recommendation method, comprising:
   acquiring basic information of a user;
   preprocessing the basic information of the user to obtain query variables corresponding to a pre-established exercise knowledge graph, wherein the preprocessing comprises discretizing user characteristics in the basic information of the user to represent the user characteristics as low-dimensional embedding vectors;
   creating a query statement based on the query variables, and querying the pre-established exercise knowledge graph through the query statement to obtain a target exercise mode list comprising exercise modes, and an evaluation attribute list comprising evaluation attributes and corresponding to the target exercise mode list, each of the evaluation attributes indicating an attribute index for evaluating a corresponding exercise mode;
   determining at least one exercise program according to the target exercise mode list and the evaluation attribute list, each exercise program in the at least one exercise program comprising at least one exercise mode and a recommended exercise duration corresponding to the at least one exercise mode;
   performing ranking processing on the at least one exercise program according to the evaluation attribute list to obtain a ranking result;
   recommending at least one target exercise program according to the ranking result.

2. The method according to claim 1, wherein said creating a query statement based on the query variables, and querying the pre-established exercise knowledge graph through the query statement to obtain a target exercise mode list comprising exercise modes, and an evaluation attribute list comprising evaluation attributes corresponding to the target exercise mode list comprises:

creating at least one query statement according to the query variables;

querying the exercise knowledge graph according to each query statement in the at least one query statement respectively to obtain the target exercise mode list and the evaluation attribute list corresponding to the target exercise mode list.

3. The method according to claim 2, wherein the basic information of the user comprises: a target disease type of the user, a target user attribute of the user, and a physical activity level assessment result of the user, and wherein said creating at least one query statement according to the query variables comprises:

acquiring a physical activity level assessment result of the user;

in response to the physical activity level assessment result of the user being a high level, creating a first query statement using the target user attribute and the target disease type as query conditions;

in response to the physical activity level assessment result of the user being a medium level or below, creating a first query statement using the target user attribute and the target disease type as query conditions, and creating a second query statement using the physical activity level assessment result of the user as a query condition.

4. The method according to claim 3, wherein the exercise knowledge graph comprises a first relationship between a user attribute entity and an exercise category entity, and a second relationship between an exercise category entity and a disease type entity, and, wherein said querying the exercise knowledge graph according to each query statement in the at least one query statement respectively to obtain the target exercise mode list and the evaluation attribute list corresponding to the target exercise mode list comprises:

in response to the physical activity level assessment result of the user being a high level, querying the first relationship and the second relationship in the exercise knowledge graph according to the first query statement to obtain the target exercise mode list;

in response to the physical activity level assessment result of the user being a medium level or below, querying the first relationship and the second relationship in the exercise knowledge graph according to the first query statement to obtain an initial exercise mode list, and querying the exercise knowledge graph according to the second query statement to obtain exercise modes that satisfy the physical activity level assessment result of the user in the initial exercise mode list as the target exercise mode list;

acquiring the evaluation attribute list corresponding to the target exercise mode list.

5. The method according to claim 1, wherein said determining at least one exercise program according to the target exercise mode list and the evaluation attribute list comprises:

acquiring a target calorie consumption of the user;

combining the exercise modes comprised in the target exercise mode list to obtain an exercise combination result, the exercise combination result comprising at least one exercise mode;

extracting an evaluation attribute in the evaluation attribute list corresponding to the exercise combination result according to the exercise combination result;

determining a recommended time combination corresponding to the exercise combination result according to the evaluation attribute corresponding to the exercise combination result and the target calorie consumption, the recommended time combination comprising a recommended exercise duration corresponding to each exercise mode in the exercise combination result;

combining the exercise combination result with the recommended time combination corresponding to the exercise combination result as the at least one exercise program.

6. The method according to claim 5, wherein each evaluation attribute comprises a per unit calorie consumption corresponding to a respective exercise mode, and said determining a recommended time combination corresponding to the exercise combination result according to the evaluation attribute corresponding to the exercise combination result and the target calorie consumption comprises:

determining the recommended time combination corresponding to the exercise combination result according to a sum of products of per unit calorie consumptions corresponding to exercise modes comprised in the exercise combination result and respective recommended exercise durations being equal to the corresponding target calorie consumption.

7. The method according to claim 1, wherein said determining at least one exercise program according to the target exercise mode list and the evaluation attribute list comprises:

acquiring an exercise frequency of the user during an exercise planning period;

combining the exercise modes comprised in the target exercise mode list to obtain an exercise combination result, the exercise combination result comprising at least one exercise mode;

determining a maximum activity amount and a minimum activity amount to which the exercise planning period corresponds;

determining a time array according to the maximum activity amount and the minimum activity amount, the time array comprising the exercise frequency and a recommended exercise duration corresponding to the exercise frequency;

allocating the time array to the exercise combination result according to the exercise frequency in the exercise planning period to obtain the at least one exercise program.

8. The method according to claim 5, wherein said combining the exercise modes comprised in the target exercise mode list to obtain an exercise combination result comprises:

according to a physical activity level assessment result of the user, acquiring a preset number of exercise modes corresponding to the physical activity level assessment result of the user from the exercise modes comprised in the target exercise mode list as the exercise combination result.

9. The method according to claim 1, wherein the evaluation attribute list comprises a plurality of evaluation attributes corresponding to the exercise modes, and said performing ranking processing on the at least one exercise program according to the evaluation attribute list comprises:

determining an exercise risk level of the user according to the basic information of the user;

ranking the at least one exercise program according to the plurality of evaluation attributes and the exercise risk level.

10. The method according to claim 9, wherein said ranking the at least one exercise program according to the plurality of evaluation attributes and the exercise risk level comprises:
acquiring a weight coefficient corresponding to each evaluation attribute in the plurality of evaluation attributes of each exercise mode;
calculating a weighted sum based on weight coefficients corresponding to the plurality of evaluation attributes and values corresponding to the plurality of evaluation attributes to obtain a first multiplication result;
multiplying a value of the exercise risk level corresponding to said each exercise mode by a weight coefficient corresponding to the exercise risk level to obtain a second multiplication result;
taking a sum of the first multiplication result and the second multiplication result as an evaluation index of said each exercise mode in the at least one exercise program;
determining a comprehensive evaluation index of each exercise program according to the evaluation index for each exercise mode and a weight coefficient corresponding to each exercise mode;
ranking the at least one exercise program according to the comprehensive evaluation index of each exercise program.

11. The method according to claim 9, wherein said ranking the at least one exercise program according to the plurality of evaluation attributes and the exercise risk level comprises:
acquiring a weight coefficient corresponding to each evaluation attribute in the plurality of evaluation attributes of each exercise mode;
calculating a weighted sum based on weight coefficients corresponding to the plurality of evaluation attributes and values corresponding to the plurality of evaluation attributes to obtain a first multiplication result;
multiplying a value of the exercise risk level corresponding to said each exercise mode by a weight coefficient corresponding to the exercise risk level to obtain a second multiplication result;
multiplying a recommended exercise duration of said each exercise mode by a weight coefficient corresponding to the recommended exercise duration to obtain a third multiplication result;
taking a sum of the first multiplication result, the second multiplication result, and the third multiplication result as an evaluation index of said each exercise mode in the at least one exercise program;
determining a comprehensive evaluation index of each exercise program according to the evaluation index of each exercise mode and a weight coefficient corresponding to each exercise mode;
ranking the at least one exercise program according to the comprehensive evaluation index of each exercise program.

12. The method according to claim 1, wherein prior to said creating a query statement based on the query variables, and querying the pre-established exercise knowledge graph through the query statement, the method further comprises:
determining an exercise risk level of the user according to the basic information of the user;
determining a range of exercise modes comprised in the target exercise mode list according to the exercise risk level.

13. The method according to claim 12, wherein said determining an exercise risk level of the user according to the basic information of the user comprises:
inputting the basic information of the user into a pre-established exercise risk classification model to obtain the exercise risk level of the user.

14. The method according to claim 1, wherein the basic information of the user comprises a target disease type, a target user attribute and a physical activity level assessment result of the user, and
wherein said acquiring the basic information of the user comprises:
acquiring the target disease type, the target user attribute and the physical activity level assessment result of the user in an electronic questionnaire manner.

15. The method according to claim 1, wherein the basic information of the user comprises a target disease type, a target user attribute and a physical activity level assessment result of the user, and
wherein said acquiring the basic information of the user comprises:
acquiring the target disease type and the target user attribute of the user through user physical examination data;
acquiring the physical activity level assessment result of the user in an electronic questionnaire manner.

16. The method according to claim 14, wherein the electronic questionnaire manner comprises at least one of a human-computer interaction presentation interface and a voice conversation mode.

17. The method according to claim 15, wherein the electronic questionnaire manner comprises at least one of a human-computer interaction presentation interface and a voice conversation mode.

18. An exercise recommendation apparatus, comprising:
an information acquirer configured to acquire basic information of a user;
a graph querier configured to preprocessing the basic information of the user to obtain query variables corresponding to a pre-established exercise knowledge graph, and creating a query statement based on the query variables, and querying the pre-established exercise knowledge graph through the query statement to obtain a target exercise mode list comprising exercise modes, and an evaluation attribute list comprising evaluation attributes and corresponding to the target exercise mode list, each evaluation attribute indicating an attribute index for evaluating a corresponding exercise mode, wherein the preprocessing comprises discretizing user characteristics in the basic information of the user to represent the user characteristics as low-dimensional embedding vectors;
a program determiner configured to determine at least one exercise program according to the target exercise mode list and the evaluation attribute list, each exercise program in the at least one exercise program comprising at least one exercise mode and a recommended exercise duration corresponding to the at least one exercise mode;
a program ranker configured to rank the at least one exercise program according to the evaluation attribute list to obtain a ranking result;

a program recommender configured to recommend at least one target exercise program according to the ranking result.

19. An electronic device comprising a memory, a processor, and computer instructions stored on the memory and executable on the processor, implementing the method according to claim 1 when the computer instructions are executed by the processor.

20. A non-transitory computer-readable storage medium having computer instructions stored thereon, which is configured to implement the method according to claim 1 when the computer instructions are executed.

* * * * *